(12) United States Patent
Gim et al.

(10) Patent No.: US 11,103,441 B2
(45) Date of Patent: Aug. 31, 2021

(54) ORAL COMPOSITION

(71) Applicant: LG HOUSEHOLD & HEALTH CARE LTD., Seoul (KR)

(72) Inventors: So-Eun Gim, Daejeon (KR); Kyo-Tae Moon, Daejeon (KR); Won-Ho Ha, Daejeon (KR); Jae-Hyun Ahn, Daejeon (KR); In-Ho Lee, Daejeon (KR)

(73) Assignee: LG HOUSEHOLD & HEALTH CARE LTD., Seoul (KR)

( * ) Notice: Subject to any disclaimer, the term of this patent is extended or adjusted under 35 U.S.C. 154(b) by 0 days.

(21) Appl. No.: 15/567,240

(22) PCT Filed: Apr. 15, 2016

(86) PCT No.: PCT/KR2016/003945
§ 371 (c)(1),
(2) Date: Oct. 17, 2017

(87) PCT Pub. No.: WO2016/167600
PCT Pub. Date: Oct. 20, 2016

(65) Prior Publication Data
US 2018/0153789 A1 Jun. 7, 2018

(30) Foreign Application Priority Data

Apr. 17, 2015 (KR) .................. 10-2015-0054519
Dec. 23, 2015 (KR) .................. 10-2015-0184839
Apr. 14, 2016 (KR) .................. 10-2016-0045670
Apr. 14, 2016 (KR) .................. 10-2016-0045681

(51) Int. Cl.
| | |
|---|---|
| A61K 8/86 | (2006.01) |
| A61K 8/19 | (2006.01) |
| A61K 8/27 | (2006.01) |
| A61Q 11/00 | (2006.01) |
| A61K 8/362 | (2006.01) |
| A61K 8/55 | (2006.01) |
| A61K 8/73 | (2006.01) |
| A61K 8/64 | (2006.01) |

(52) U.S. Cl.
CPC .............. *A61K 8/86* (2013.01); *A61K 8/19* (2013.01); *A61K 8/27* (2013.01); *A61K 8/362* (2013.01); *A61K 8/55* (2013.01); *A61K 8/64* (2013.01); *A61K 8/731* (2013.01); *A61Q 11/00* (2013.01)

(58) Field of Classification Search
CPC .................... A61K 9/68; A61K 7/16
USPC .................................... 424/49, 52
See application file for complete search history.

(56) References Cited

U.S. PATENT DOCUMENTS

| | | | |
|---|---|---|---|
| 5,270,031 A | 12/1993 | Lim et al. | |
| 5,976,506 A | 11/1999 | Vernon | |
| 5,981,475 A * | 11/1999 | Reynolds | A61K 8/64 514/20.1 |
| 6,485,708 B1 * | 11/2002 | Winston | A61K 8/19 424/49 |
| 6,685,920 B2 * | 2/2004 | Baig | A23G 4/126 424/49 |
| 2010/0135921 A1 | 6/2010 | Hughes et al. | |
| 2011/0027198 A1 * | 2/2011 | Sharma | A61Q 11/00 424/55 |
| 2012/0308488 A1 | 12/2012 | Pilch et al. | |
| 2013/0078197 A1 | 3/2013 | Mello et al. | |
| 2014/0079750 A1 * | 3/2014 | Li | A61K 8/19 424/401 |

FOREIGN PATENT DOCUMENTS

| | | | |
|---|---|---|---|
| JP | H6-29169 B2 | 4/1994 | |
| JP | 2004-59583 A | 2/2004 | |
| JP | 2006-347987 | * 12/2006 | ............... A61K 8/00 |
| KR | 10-0169140 B1 | 1/1999 | |
| KR | 10-2001-0041671 A | 5/2001 | |

(Continued)

OTHER PUBLICATIONS

International Search Report for PCT/KR2016/003945 (PCT/ISA/210) dated Jul. 27, 2016.

(Continued)

*Primary Examiner* — Walter E Webb
(74) *Attorney, Agent, or Firm* — Birch, Stewart, Kolasch & Birch, LLP

(57) ABSTRACT

The present disclosure related to an oral composition, and more particularly, to an oral composition for reducing tooth sensitivity. More specifically, the oral composition contains zinc and a copper salt capable of occluding dental tubules by agglomerating proteins, contributing to the reduction effect of tooth sensitivity, and to maintain this, allows a water soluble or alcohol soluble polymer to coat the dental tubules and be maintained for a long time, thereby solving the main cause of tooth sensitivity, as a result, providing an effect on the prevention or reduction of symptoms of tooth sensitivity in a short time. Furthermore, the oral composition according to the present disclosure contains a copper salt or a zinc salt which reacts with dental tubule fluid to form a protein complex, and contains dicarboxylic acid or its salt which reacts with an inorganic matter such as calcium to form a complex to induce occlusion of dental tubules and dramatically increase the occlusion effect, producing an effect on efficient prevention or reduction of tooth sensitivity symptoms in a short time. In addition, the oral composition according to the present disclosure contains dicarboxylic acid and its salt which forms a calcium complex in the mouth to induce occlusion of dental tubules, and further contains a partially soluble calcium salt and/or phosphate to dramatically increase the occlusion effect of the dental tubules, producing an effect on the efficient prevention or reduction of tooth sensitivity symptoms in a short time.

3 Claims, 12 Drawing Sheets

(56) References Cited

FOREIGN PATENT DOCUMENTS

| KR | 10-2013-00496340 A | 5/2013 | | |
|---|---|---|---|---|
| KR | 10-2013-0083556 A | 7/2013 | | |
| RU | 2139034 C1 | 10/1999 | | |
| RU | 2011117019 A | 1/2013 | | |
| WO | WO 99/44570 A1 | 9/1999 | | |
| WO | WO 2009/106972 | * | 9/2009 | ............. A61Q 11/00 |
| WO | WO 2012/057739 A1 | 5/2012 | | |
| WO | WO 2012/099304 A1 | 7/2012 | | |
| WO | WO2014056824 | * | 4/2014 | ............... A61K 8/19 |

OTHER PUBLICATIONS

Amaechi, B.T., "Remineralization Therapies for Initial Caries Lesions," Current Oral Health Reports, Apr. 9, 2015, vol. 2, pp. 95-101, Abstract, p. 98, left column, first paragraph, p. 99, right column, second paragraph.

Miglani, S., et al., "Dentin hypersensitivity: Recent trends in management" J Conserv Dent., Oct.-Dec. 2010, vol. 13, No. 4, pp. 218-224, Abstract, pp. 4-5/11.

Zero, D.T., "Dentifrices, mouthwashes, and remineralization/caries arrestment strategies," BMC Oral Health, 2006, vol. 6(Suppl 1): S9, pp. 1-13, p. 8 of 13 left column, p. 9 of 13 right column.

* cited by examiner

EXAMPLE 1
-DENTAL TUBULE OCCLUSION CAPABILITY

EXAMPLE 2
-DENTAL TUBULE OCCLUSION CAPABILITY

EXAMPLE 3
-DENTAL TUBULE OCCLUSION CAPABILITY

EXAMPLE 4
-DENTAL TUBULE OCCLUSION CAPABILITY

EXAMPLE 5
-DENTAL TUBULE OCCLUSION CAPABILITY

EXAMPLE 6
-DENTAL TUBULE OCCLUSION CAPABILITY

EXAMPLE 7
-DENTAL TUBULE OCCLUSION CAPABILITY

EXAMPLE 8
-DENTAL TUBULE OCCLUSION CAPABILITY

EXAMPLE 9
-DENTAL TUBULE OCCLUSION CAPABILITY

COMPARATIVE EXAMPLE 1
-DENTAL TUBULE OCCLUSION CAPABILITY

COMPARATIVE EXAMPLE 2
-DENTAL TUBULE OCCLUSION CAPABILITY

EXAMPLE 10
-DENTAL TUBULE OCCLUSION CAPABILITY

EXAMPLE 11
-DENTAL TUBULE OCCLUSION CAPABILITY

EXAMPLE 12
-DENTAL TUBULE OCCLUSION CAPABILITY

EXAMPLE 13
-DENTAL TUBULE OCCLUSION CAPABILITY

EXAMPLE 14
-DENTAL TUBULE OCCLUSION CAPABILITY

EXAMPLE 15
-DENTAL TUBULE OCCLUSION CAPABILITY

COMPARATIVE EXAMPLE 3
-DENTAL TUBULE OCCLUSION CAPABILITY

COMPARATIVE EXAMPLE 4
-DENTAL TUBULE OCCLUSION CAPABILITY

COMPARATIVE EXAMPLE 5
-DENTAL TUBULE OCCLUSION CAPABILITY

COMPARATIVE EXAMPLE 6
-DENTAL TUBULE OCCLUSION CAPABILITY

COMPARATIVE EXAMPLE 7
-DENTAL TUBULE OCCLUSION CAPABILITY

COMPARATIVE EXAMPLE 8
-DENTAL TUBULE OCCLUSION CAPABILITY

COMPARATIVE EXAMPLE 9
-DENTAL TUBULE OCCLUSION CAPABILITY

EXAMPLE 16
-DENTAL TUBULE OCCLUSION CAPABILITY

EXAMPLE 17
-DENTAL TUBULE OCCLUSION CAPABILITY

EXAMPLE 18
-DENTAL TUBULE OCCLUSION CAPABILITY

EXAMPLE 19
-DENTAL TUBULE OCCLUSION CAPABILITY

EXAMPLE 20
-DENTAL TUBULE OCCLUSION CAPABILITY

EXAMPLE 21
-DENTAL TUBULE OCCLUSION CAPABILITY

EXAMPLE 23
-DENTAL TUBULE OCCLUSION CAPABILITY

EXAMPLE 24
-DENTAL TUBULE OCCLUSION CAPABILITY

EXAMPLE 25
-DENTAL TUBULE OCCLUSION CAPABILITY

EXAMPLE 26
-DENTAL TUBULE OCCLUSION CAPABILITY

EXAMPLE 27
-DENTAL TUBULE OCCLUSION CAPABILITY

EXAMPLE 28
-DENTAL TUBULE OCCLUSION CAPABILITY

EXAMPLE 29
-DENTAL TUBULE OCCLUSION CAPABILITY

EXAMPLE 30
-DENTAL TUBULE OCCLUSION CAPABILITY

EXAMPLE 31
-DENTAL TUBULE OCCLUSION CAPABILITY

EXAMPLE 32
-DENTAL TUBULE OCCLUSION CAPABILITY

COMPARATIVE EXAMPLE 10
-DENTAL TUBULE OCCLUSION CAPABILITY

COMPARATIVE EXAMPLE 11
-DENTAL TUBULE OCCLUSION CAPABILITY

COMPARATIVE EXAMPLE 12
-DENTAL TUBULE OCCLUSION CAPABILITY

COMPARATIVE EXAMPLE 13
-DENTAL TUBULE OCCLUSION CAPABILITY

COMPARATIVE EXAMPLE 14
-DENTAL TUBULE OCCLUSION CAPABILITY

COMPARATIVE EXAMPLE 15
-DENTAL TUBULE OCCLUSION CAPABILITY

ORAL COMPOSITION

FIELD

The present disclosure relates to an oral composition, and more particularly, to an oral composition for reducing tooth sensitivity.

The present application claims priority to Korean Patent Application No. 10-2015-0054519 filed in the Republic of Korea on Apr. 17, 2015, Korean Patent Application No. 10-2015-0184839 filed in the Republic of Korea on Dec. 23, 2015, Korean Patent Application No. 10-2016-0045670 filed in the Republic of Korea on Apr. 14, 2016, and Korean Patent Application No. 10-2016-0045681 filed in the Republic of Korea on Apr. 14, 2016, the disclosure of which is incorporated herein by reference.

BACKGROUND

Symptom of tooth sensitivity is a feeling of sensitivity occurring when the exposed dentin comes into contact with cold air or pungent foods, and the main cause of this symptom is exposure of many tubules present in the enamel of the tooth to the outside. The tooth sensitivity symptom appears with a wide range of pains from mild to severe that continue long. In addition, because teeth do not regrow according to the nature, administration of an analgestic or antiphlogistic cannot be a key solution to tooth sensitivity, so many therapies have been developed to reduce tooth sensitivity symptoms.

The most common method for reducing symptoms of tooth sensitivity is to disturb neurotransmission, and a method which disturbs the ion balance of sodium (Na) and potassium (K) to prevent the transfer of an external stimulus to the brain was widely used in the past. It is general to reduce tooth sensitivity using potassium nitrate ($KNO_3$) being employed by many companies including Glaceau as a source of potassium. However, because the ion disturbance lasts for a short time, attempts to solve this problem are needed.

To reduce symptoms of tooth sensitivity, technology for reducing symptoms of tooth sensitivity using arginine and calcium carbonate was designed by ROBINSON, Richard (WO2012-057739). However, because this technology could not bring completely reduced symptoms of tooth sensitivity to consumers, there is a need for development of technology for reducing symptoms of tooth sensitivity in a short time. Furthermore, there is technology for occluding the dental tubules using an acrylic polymer through UV crosslinking, but this requires dental procedures.

Treatment of tooth sensitivity symptoms largely includes two methods: a dental tubule sealing method and a desensitization method of pulpal sensory nerve. The dental tubule sealing method is a method which plugs the exposed dental tubules with resin or restores the lost enamel by fluoride coating, and the desensitization method of pulpal sensory nerve is therapy which makes the nerves less sensitive to sore pain by deliberately increasing the content of calcium ions when considering that neurotransmission is controlled by an optimum ratio of sodium ions and potassium ions. However, there is the inconvenience of having to go to the dentists to receive such professional therapy services.

Accordingly, there is an urgent need for development of products that can be readily accessed by ordinary people, effectively occlude the dental tubules and maintain the occluded dental tubules, and allows users to experience reduced symptoms of tooth sensitivity in a short time.

DISCLOSURE

Technical Problem

The present disclosure is directed to providing an oral composition for preventing or reducing tooth sensitivity symptoms by effectively occluding the dental tubules.

Further, the present disclosure is directed to providing a method for preventing or reducing tooth sensitivity symptoms, including applying the oral composition to a subject in need thereof.

Further, the present disclosure is directed to providing the use of active ingredients for preparing a composition for preventing or reducing tooth sensitivity symptoms.

Technical Solution

To achieve the above objects, the present disclosure provides an oral composition for preventing or reducing tooth sensitivity containing i) a copper salt or a zinc salt; ii) a water soluble or alcohol soluble polymer; or iii) a mixture of i) and ii) as an active ingredient.

Further, the present disclosure provides a method for preventing or reducing tooth sensitivity symptoms, including applying a composition to a subject in need thereof, the composition containing i) a copper salt or a zinc salt; ii) a water soluble or alcohol soluble polymer; or iii) a mixture of i) and ii) as an active ingredient.

Further, the present disclosure provides the use of i) a copper salt or a zinc salt; ii) a water soluble or alcohol soluble polymer; or iii) a mixture of i) and ii) for preparing a composition for preventing or reducing tooth sensitivity symptoms.

The present disclosure provides an oral composition for preventing or reducing tooth sensitivity containing i) a copper salt or a zinc salt; and/or ii) dicarboxylic acid or its salt as an active ingredient. Particularly, the inventors found that a composition containing both i) a copper salt or a zinc salt; and ii) dicarboxylic acid or its salt as active ingredients has a synergetic effect when compared to compositions containing each active ingredient separately, and accordingly, preferably there is provided an oral composition for preventing or reducing tooth sensitivity containing i) a copper salt or a zinc salt; and ii) dicarboxylic acid or its salt as active ingredients.

Further, the present disclosure provides a method for preventing or reducing tooth sensitivity symptoms including applying a composition to a subject in need thereof, the composition containing i) a copper salt or a zinc salt; and/or ii) dicarboxylic acid or its salt as an active ingredient.

Further, the present disclosure provides the use of i) a copper salt or a zinc salt; and/or ii) dicarboxylic acid or its salt for preparing a composition for preventing or reducing tooth sensitivity symptoms.

The present disclosure provides an oral composition for preventing or reducing tooth sensitivity containing i) dicarboxylic acid or its salt; and ii) a partially soluble calcium salt as active ingredients, and preferably an oral composition for preventing or reducing tooth sensitivity wherein the composition further contains phosphate as an active ingredient.

Further, the present disclosure provides a method for preventing or reducing tooth sensitivity symptoms, including applying a composition to a subject in need thereof, the composition containing i) dicarboxylic acid or its salt; and ii) a partially soluble calcium salt as active ingredients, and preferably a method for preventing or reducing tooth sensitivity symptoms including applying the composition further containing phosphate as an active ingredient to a subject in need thereof.

Further, the present disclosure provides the use of i) dicarboxylic acid or its salt; and ii) a partially soluble calcium salt for preparing a composition for preventing or reducing tooth sensitivity symptoms, and preferably the use of i) dicarboxylic acid or its salt; ii) a partially soluble calcium salt; and phosphate.

The inventors recognized that it is important to occlude the exposed dental tubules and protect them from external stimuli to prevent or reduce tooth sensitivity, and found the superior dental tubule occlusion efficacy of the material and completed the invention.

Dentin is a hard tissue that makes up the majority of dental tissues, and has dental tubules or minute tubes distributed throughout the whole enamel.

Dendritic cells in the dental pulp are distributed from the dentin to the enamel to form dental tubules, and spaces between dental tubules and dendritic cells are filled with enamel fluid.

The term "tooth sensitivity" as used therein includes, but is not limited to, all phenomena involving acute and temporary or continuous pains to an external stimulus independent of tooth decay or other pathological causes. The external stimulus generally refers to a temperature stimulus, and symptoms are usually complained due to cold temperature stimuli, and pains may also arise from hot temperature. In addition to temperature stimuli, pains may be caused by stimuli such as dry teeth, contact with external materials, and osmosis through sweet or sour foods. Such pains may appear throughout the whole teeth and on a limited, particular part such as the upper or lower jaw or right or left side, and there may be accompanying dentin hyperesthesia, dental caries, and dental pulp inflammation.

The cause of tooth sensitivity symptoms is thought to be the exposure of the entrance of dental tubules.

When the enamel or cementum is destroyed and the entrance of dental tubules is exposed to the outside, stimuli are transmitted to the dental pulp by the dendritic cells of dental tubules, nerves and enamel fluid, causing pains.

The term "prevent" as used therein can be understood in broad sense as avoiding tooth sensitivity symptoms and sensitive tooth symptoms such as the above before they occur.

The term "reduce" as used therein refers to mitigating or relieving tooth sensitivity symptoms and sensitive tooth symptoms such as the above, and can be understood in broad sense as alleviation, prevention, and treatment.

The term "enhance" as used therein can be understood in broad sense as bringing back to close to the original condition by treating tooth sensitivity symptoms and sensitive tooth symptoms.

[An oral composition for preventing or reducing tooth sensitivity, containing i) a copper salt or a zinc salt; ii) a water soluble or alcohol soluble polymer; or iii) a mixture of i) and ii) as an active ingredient].

In the present disclosure, to avoid the repeated disclosure, hereinafter the description of an oral composition for preventing or reducing tooth sensitivity containing i) a copper salt or a zinc salt; ii) a water soluble or alcohol soluble polymer; or iii) a mixture of i) and ii) as an active ingredient' is equally applied to 'a method for preventing or reducing tooth sensitivity symptoms including applying a composition containing i) a copper salt or a zinc salt; ii) a water soluble or alcohol soluble polymer; or iii) a mixture of i) and ii) as an active ingredient' and 'the use of i) a copper salt or a zinc salt; ii) a water soluble or alcohol soluble polymer; or iii) a mixture of i) and ii) for preparing a composition for preventing or reducing tooth sensitivity symptoms'.

When the oral composition is applied in the mouth, the copper salt or zinc salt forms a protein complex (precipitated) in the mouth with proteins or enzymes present in the mouth including, but not limited to, for example, mucin, histatin, cystatin, peroxidase, lactoferrin, casein, amylase, lysozyme, globulin, mucous membrane glycoprotein, albumin, oligo and polypeptide. The diameter of the protein complex is 7 μm or less, i.e., 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7 μm or less, and preferably 5 μm or less. Because the mean diameter of the dental tubules is from 3 to 7 μm, the protein complex formed in the mouth can be easily introduced into the dental tubules.

Further, the oral composition reacts with dental tubule fluid to form a protein complex.

Further, because the complex is a protein agglomerate, the complex forms a strong secondary bond or hydrogen bond with proteins in the dental tubules to generate a electrostatic attraction force with the components of teeth in electrically non-organized state by agglomeration of zinc ions and proteins, and due to having a high affinity with the dental pulp within the dental tubules; and hydroxyapatite and proteins that are the components of the dental tubules, the complex can stay in the dental tubules for a long time, and ultimately, occlude the dental tubules effectively to prevent or reduce tooth sensitivity symptoms.

In the present disclosure, the copper salt or zinc salt is present in an amount of 0.02 to 5 wt % based on the total weight of the composition, i.e., 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5 wt %, preferably 0.05 to 3 wt %, and more preferably 0.05 to 1 wt %. Less than 0.02 wt % of the copper salt or zinc salt is insufficient to generate a complex with proteins and does not work on tooth sensitivity reduction, and more than 5 wt % of the copper salt or zinc salt may cause irritation in the mouth.

The copper salt used in the present disclosure includes, but is not limited to, for example, copper (I) chloride, copper (II) chloride, copper (I) iodide, copper sulfate, copper nitrate, copper pyrophosphate, copper chlorophyll, copper gluconate or mixtures thereof.

The zinc salt used in the present disclosure include, but is not limited to, for example, zinc nitrate, zinc chloride, zinc sulfate, zinc phosphate, zinc molybdate, zinc acetate, zinc stearate, zinc carbonate, zinc fluoride, zinc hydroxide, zinc oxalate or mixtures thereof.

Further, the present disclosure may include a water soluble or alcohol soluble polymer to increase the dental tubule occlusion effect.

The term "pharmaceutical agent" as used herein refers to all substances included in the oral composition to enhance or improve tooth health. The pharmaceutical agent includes, for example, decay preventing agents, pyorrhea preventing agents, tooth whitening agents, odor preventing agents, plaque removing agents and tooth sensitivity preventing agents.

The inventors searched for substances to solve the problems of conventional pharmaceutical agents for tooth sensitivity because the conventional pharmaceutical agents do not stay on the tooth surface for a long time and their effects do not last long, and work in the manner of plugging dental tubules by forming an insoluble salt, as a consequence, attachment of insoluble salts to teeth is poor and particles filled in the dental tubules are released again, resulting in reduced effect, and they found that an oral composition including a water soluble or alcohol soluble polymer has an effect on the surface coverage of dental tubules, thereby effectively preventing or reducing tooth sensitivity, and the use of polymers having a high adhesive strength of the polymers and functional groups that form strong secondary bonds with the components of teeth can improve interactions within the polymers and interactions with teeth (as substrate), and make less vulnerable to detachment from the teeth, enhancing the tooth attachment characteristics, and besides, the water soluble and alcohol soluble polymer captures drugs in the form of chains, thereby allowing attachment to the dental tissues or dental tubule tissues and extending the duration in which the pharmaceutical agent is attached to teeth.

The water soluble or alcohol soluble polymer has an affinity with, but not limited to, hydroxyapatite having hydrophilicity. The affinity polymer should be dissolved in water or a polar solvent such as alcohol, for example, ethanol. Thus, the water soluble or alcohol soluble polymer includes polymers with functionality having a functional group such as carboxylic acid, hydroxy, pyrrole, pyridine, amine, amino acid, imine, peptide, carbonate, ester, and ether.

The water soluble or alcohol soluble polymer includes, but is not limited to, for example, a polyethyleneglycol/polypropyleneglycol copolymer, a polyethyleneglycol/polypropyleneglycol/polyethyleneglycol triblock copolymer, polyethyleneglycol, polypropyleneglycol, polypyrrole, polyvinylpyrrolidone, polypyridine, hydroxymethylcellulose, hydroxypropylmethylcellulose, hydroxypropylcellulose, hydroxyethylcellulose, carboxymethylcellulose, ethylcellulose, methylcellulose, cellulose or mixtures thereof, and the biocompatible polymer has an affinity with hydroxyapatite that is the component of dental tubules and proteins of the dental tubules, and can stay in the mouth for a prolonged period of time.

In the present disclosure, the water soluble or alcohol soluble polymer is present in an amount of 0.1 to 15 wt % based on the total weight of the composition, i.e., 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.1, 10.2, 10.3, 10.4, 10.5, 10.6, 10.7, 10.8, 10.9, 11, 11.1, 11.2, 11.3, 11.4, 11.5, 11.6, 11.7, 11.8, 11.9, 12, 12.1, 12.2, 12.3, 12.4, 12.5, 12.6, 12.7, 12.8, 12.9, 13, 13.1, 13.2, 13.3, 13.4, 13.5, 13.6, 13.7, 13.8, 13.9, 14, 14.1, 14.2, 14.3, 14.4, 14.5, 14.6, 14.7, 14.8, 14.9, 15 wt %, preferably 0.3 to 10 wt %, and more preferably 0.5 to 5 wt %. When the polymer content is less than 0.1 wt %, the residence characteristics in the body are degraded, and when the polymer content is more than 15 wt %, it fails to satisfy the property requirements for oral hygiene products.

In the present disclosure, the molecular weight of the water soluble or alcohol soluble polymer is from 8,000 to 9,000,000, and preferably from 600,000 to 4,000,000. When the molecular weight of the water soluble or alcohol soluble polymer is more than 9,000,000, the viscosity is too high at the time of manufacture, making difficult to manufacture, and when the molecular weight of the water soluble or alcohol soluble polymer is less than 8,000, the strength of adhesion to teeth is too low, failing to show the adhesive characteristics of the polymer to teeth.

Further, the present disclosure may include an oral composition containing the copper salt or zinc salt as an active ingredient to induce occlusion of dental tubules and a water soluble or alcohol soluble polymer to increase the occlusion effect of the occluded dental tubules.

In the present disclosure, the copper salt or zinc salt is mixed with the water soluble or alcohol soluble polymer at a weight ratio of 0.02~5:0.1~15, i.e., 0.02~1:0.1~15, 0.02~2:0.1~15, 0.02~3:0.1~15, 0.02~4:0.1~15, 0.02~5:0.1~15, 0.02~5:0.1~1, 0.02~5:0.1~2, 0.02~5:0.1~3, 0.02~5:0.1~4, 0.02~5:0.1~5, 0.02~5:0.1~6, 0.02~5:0.1~6, 0.02~5:0.1~7, 0.02~5:0.1~8, 0.02~5:0.1~9, 0.025:0.1~10, 0.025:0.1~11, 0.025:0.1~12, 0.025:0.1~13, 0.025:0.1~14, 0.02~5:0.1~15, and preferably 0.05~3:0.3~10, i.e., 0.05~1:0.3~10, 0.05~2:0.3~10, 0.05~3:0.3~10, 0.05~1:0.3~1, 0.05~1:0.3~2, 0.05~1:0.3~3, 0.05~1:0.3~4, 0.05~1:0.3~5, 0.05~1:0.3~6, 0.05~1:0.3~7, 0.05~1:0.3~8, 0.05~1:0.3~9, 0.05~1:0.3~10, to produce a synergetic effect on the prevention or reduction of tooth sensitivity symptoms. The weight ratio out of the range has problems with formulation and product stability, and fails to obtain a desired effect on tooth sensitivity reduction.

Accordingly, the oral composition of the present disclosure has a superior dental tubule occlusion capability, and can efficiently prevent or reduce tooth sensitivity symptoms in a short time.

The oral composition according to the present disclosure may further contain additives including, but is not limited to, for example, wetting agents, abrasives, pharmaceutical agent, sweetening agents, pH adjusters, preservatives, binders, flavorings, whitening agents, foaming agents, or purified water, to ensure optimum formulation and formulation stability, increase a desired effect, and enhance usage preference.

The wetting agent includes, but is not limited to, for example, concentrated glycerin, glycerin, an aqueous sorbitol solution or an aqueous non-crystalline sorbitol solution, used alone or in combination, and may be present in an amount of 1 to 60 wt % based on the total weight of the oral composition, but is not limited thereto.

The abrasive includes, but is not limited to, for example, precipitated silica, silica gel, zirconium silicate, dibasic calcium phosphate, anhydrous dibasic calcium phosphate, hydrated alumina, calcium carbonate, light calcium carbonate, heavy calcium carbonate, calcium pyrophosphate, insoluble metaphosphate or aluminum silicate. Generally, the abrasive may be present in an amount of 1 to 60 wt % based on the total weight of the oral composition, but is not limited thereto.

The water soluble or alcohol soluble polymer is mixed with the pharmaceutical agent at a weight ratio of 0.1~15:0.005~5, i.e., 0.1~1:0.05~5, 0.1~2:0.05~5, 0.1~3:0.05~5, 0.1~4:0.05~5, 0.1~5:0.05~5, 0.1~6:0.05~5, 0.1~7:0.05~5, 0.1~8:0.05~5, 0.1~9:0.05~5, 0.1~10:0.05~5, 0.1~11:0.05~5, 0.1~12:0.05~5, 0.1~13:0.05~5, 0.1~14:0.05~5, 0.1~15:0.05~5, 0.1~1:0.05~1, 0.1~1:0.05~2, 0.1~1:0.05~3, 0.1~1:0.05~4, 0.1~1:0.05~5, and preferably 0.3~10:0.01~3, i.e., 0.3~1:0.01~3, 0.3 2:0.01~3, 0.3~3:0.01~3, 0.3 4:0.01~3, 0.3~5:0.01~3, 0.3~5:0.01~3, 0.3~6:0.01~3, 0.3~7:0.01~3, 0.3~8:0.01~3, 0.3~9:0.01~3, 0.3~10:0.01~3, 0.3~10:0.01~1, 0.3~1:0.01~2, 0.3~1:0.01~3, and the mixing at the weight ratio overcame the drawback of conventional pharmaceutical agents, namely, the conventional pharmaceutical agents do not stay on the tooth surface for a long time and their effects do not last long.

The pharmaceutical agent includes, but is not limited to, for example, sodium fluoride, sodium monofluorophosphate, stannous fluoride, chlorohexidine, allantoin chlorohydroxyaluminate, aminocaproic acid, pyridoxine hydrochloride, tocopherol acetate, or enzymes, used alone or in combination.

In the present disclosure, the pharmaceutical agent is present in an amount of 0.005 to 5 wt % based on the total weight of the composition, i.e., 0.005, 0.01, 0.015, 0.02, 0.025, 0.03, 0.035, 0.4, 0.045, 0.05, 0.055, 0.06, 0.065, 0.07, 0.075, 0.08, 0.085, 0.09, 0.095, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5 wt %, preferably 0.01 to 2 wt %, and more preferably 0.3 to 1 wt %. Less than 0.005 wt % of the pharmaceutical agent fails to effectively produce its effect, and more than 5 wt % of the pharmaceutical agent fails to produce a notable effect compared to the content used.

The sweetening agent includes, but is not limited to, for example, sodium saccharin, xylitol, erythritol, or aspartame, and generally, the sweetening agent may be present in an amount of 0.05 to 0.5 wt % based on the total weight of the oral composition, but is not limited thereto.

The pH adjuster includes, but is not limited to, for example, sodium phosphate, disodium phosphate, citric acid, sodium citrate, succinic acid, sodium succinate, tartaric acid or sodium tartrate, and the preferred pH is from 5 to 10, i.e., 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.

The preservative includes, but is not limited to, for example, benzoic acid, methylparaben, propylparaben, or sodium benzoate, used alone or in combination.

The binder includes, but is not limited to, for example, guar gum, pectin, carboxyvinylpolymer, sodium alginate, laponite, carbomer, carrageenan, xanthan gum, or alginates. Generally, the binder may be present in an amount of 0.1 to 3 wt % based the total weight of the oral composition, and preferably 0.5 to 2 wt %, but is not limited thereto.

The flavoring includes, but is not limited to, for example, peppermint oil, spearmint oil, carvone or menthol, used alone or in combination, and preferably a flavoring mixture at a predetermined mix ratio may be mixed with anise oil in optimum amounts.

The whitening agent includes titanium oxide, and is preferably present in an amount of 0.1 to 2 wt %.

The foaming agent includes, but is not limited to, for example, an anionic surfactant such as sodium alkylsulfate and sodium lauryl sulfate, a non-ionic surfactant such as a copolymer (poloxamer) of polyoxyethylenepolyoxypropylene, polyoxyethylene hydrogenated castor oil, or polyoxyethylene sorbitan fatty acid ester. Generally, the foaming agent may be present in an amount of 0.5 to 5 wt % based on the total weight of the oral composition, and preferably 0.5 to 3.5 wt %, but is not limited thereto.

The sweetening agent includes, but is not limited to, for example, sodium saccharin, aspartame, and glycyrrhetinic acid, used alone or in combination, and may be present in an amount of 0.05 to 0.5 wt %.

The oral composition of the present disclosure may include other additive, for example, enzymes such as dextranase.

The oral composition of the present disclosure may include a remaining amount of water, preferably purified water, in addition to the active ingredients and the additives.

The oral composition according to the present disclosure may have formulations such as, for example, toothpastes, mouth washes, sprays, mouth rinses, gums, candies, solutions for mouth cleaning, and tooth whitening products, but is not limited thereto, and any formulation that can bring into contact with the oral tissues after introduction in the mouth is available without limitations, and the oral composition may be formulated by a general means known to those skilled in the art.

Further, the present disclosure provides a method for preventing or reducing tooth sensitivity symptoms, including applying a composition to a subject in need thereof, the composition containing i) a copper salt or a zinc salt; ii) a water soluble or alcohol soluble polymer; or iii) a mixture of i) and ii) as an active ingredient.

The subject may be preferably a mammal, and more preferably a human, and preferably the applying refers to applying in the mouth.

An Oral Composition for Preventing or Reducing Tooth Sensitivity Containing i) a Copper Salt or a Zinc Salt; and ii) Dicarboxylic Acid or its Salt as Active Ingredients In the present disclosure, to avoid the repeated disclosure, hereinafter the description of 'an oral composition for preventing or reducing tooth sensitivity containing i) a copper salt or a zinc salt; and ii) dicarboxylic acid or its salt as active ingredients' is equally applied to 'a method for preventing or reducing tooth sensitivity symptoms including applying a composition containing i) a copper salt or a zinc salt; and ii) dicarboxylic acid or its salt as active ingredients' and 'the use of i) a copper salt or a zinc salt; and ii) dicarboxylic acid(dicarboxylic acid) or its salt for preparing a composition for preventing or reducing tooth sensitivity symptoms'.

When the oral composition is applied in the mouth, the copper salt or zinc salt forms a protein complex (precipitated) in the mouth with protein or enzyme present in the mouth including, but not limited to, for example, mucin, histatin, cystatin, peroxidase, lactoferrin, casein, amylase, lysozyme, globulin, mucous membrane glycoprotein, albumin, oligo and polypeptide. The diameter of the protein complex is 7 μm or less, i.e., 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7 μm or less, and preferably 5 μm or less. Because the mean diameter of the dental tubules is from 3 to 7 μm, the protein complex formed in the mouth can be easily introduced into the dental tubules.

Because the protein complex is a protein agglomerate, the complex forms a strong secondary bond or hydrogen bond with proteins in the dental tubules to generate a electrostatic attraction force with the components of teeth in electrically non-organized state by agglomeration of zinc ions and proteins, and due to having a high affinity with the dental pulp within the dental tubules; and hydroxyapatite and proteins that are the components of the dental tubules, the complex can stay in the dental tubules for a long time, and ultimately occlude the dental tubules effectively to prevent or reduce tooth sensitivity symptoms.

Further, the dicarboxylic acid comes into contact with calcium ions in salvia to form a calcium complex, and when considering occlusion of dental tubules, reactivity with calcium ions and attachment to teeth, preferably the dicarboxylic acid may be dicarboxylic acid having 2 to 9 carbon atoms, i.e., dicarboxylic acid having 2 carbon atoms, dicarboxylic acid having 3 carbon atoms, dicarboxylic acid having 4 carbon atoms, dicarboxylic acid having 5 carbon atoms, dicarboxylic acid having 6 carbon atoms, dicarboxylic acid having 7 carbon atoms, dicarboxylic acid having 8 carbon atoms, dicarboxylic acid having 9 carbon atoms. The calcium complex formed in the mouth can be easily introduced into the dental tubules, and particularly, the calcium complex occludes the dental tubules together with the protein complex formed with the copper salt or zinc salt, thereby occluding the dental tubules more effectively and preventing or reducing tooth sensitivity symptoms.

Further, the oral composition reacts with dental tubule fluid to form a complex.

That is, as the composition forms a protein complex and a calcium complex in the mouth, the composition has a superior dental tubule occlusion capability and produces the effect on the prevention and/or reduction of tooth sensitivity.

In the present disclosure, the copper salt or zinc salt is present in an amount of 0.02 to 5 wt % based on the total weight of the composition, i.e., 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5 wt %, preferably 0.05 to 3 wt %, and more preferably 0.05 to 1 wt %. Less than 0.02 wt % of the copper salt or zinc salt is insufficient to generate a complex with proteins and does not work on tooth sensitivity reduction, and more than 5 wt % of the copper salt or zinc salt may cause irritation in the mouth.

The copper salt used in the present disclosure includes, but is not limited to, for example, copper (I) chloride, copper (II) chloride, copper (I) iodide, copper sulfate, copper nitrate, copper pyrophosphate, copper chlorophyll, copper gluconate or mixtures thereof.

The zinc salt used in the present disclosure includes, but is not limited to, for example, zinc nitrate, zinc chloride, zinc sulfate, zinc phosphate, zinc molybdate, zinc acetate, zinc stearate, zinc carbonate, zinc fluoride, zinc hydroxide, zinc oxalate or mixtures thereof.

Preferably, the present disclosure may include dicarboxylic acid or its salt, and more preferably dicarboxylic acid having 2 to 9 carbon atoms or its salt, to increase the occlusion effect of the dental tubules.

The dicarboxylic acid includes, but is not limited to, for example, oxalic acid, malonic acid, succinic acid, glutaric acid, adipic acid, pimelic acid, suberic acid, azelaic acid or mixtures thereof, and preferably oxalic acid, malonic acid, succinic acid, glutaric acid, adipic acid or mixtures that has higher water solubility when considering superior precipitate formation.

The salt of dicarboxylic acid refers to a combination of the dicarboxylic acid and a metal ion, and the metal includes, but is not limited to, for example, sodium (Na) and potassium (K).

In the present disclosure, the dicarboxylic acid or its salt is present in an amount of 0.01 to 5 wt % based on the total weight of the composition, i.e., 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5 wt %, preferably 0.1 to 3 wt %, and more preferably 0.1 to 1 wt %. Less than 0.01 wt % of the dicarboxylic acid or its salt is insufficient to generate a calcium complex and does not work on tooth sensitivity reduction, and more than 5 wt % of the dicarboxylic acid or its salt makes it impossible for practical use due to too strong taste of the raw material itself.

In the present disclosure, the copper salt or zinc salt is mixed with the dicarboxylic acid or its salt at a weight ratio of 1:0.1~12, i.e., 1:0.1~1, 1:0.1~2, 1:0.1~3, 1:0.1~4, 1:0.1~5, 1:0.1~6, 1:0.1~7, 1:0.1~8, 1:0.1~9, 1:0.1~10, 1:0.1~11, 1:0.1~12, preferably 1:0.5~7, i.e., 1:0.5~1, 1:0.5~2, 1:0.5~3, 1:0.5~4, 1:0.5~5, 1:0.5~6, 1:0.5~7, to produce a synergetic effect on the prevention or reduction of tooth sensitivity symptoms. The weight ratio out of the range has problems with formulation and product stability, and fails to obtain a desired effect on tooth sensitivity reduction.

Accordingly, the oral composition of the present disclosure has a superior dental tubule occlusion capability, and can efficiently prevent or reduce tooth sensitivity symptoms in a short time.

The oral composition according to the present disclosure may further contain additives including, but is not limited to, for example, wetting agents, abrasives, pharmaceutical agent, sweetening agents, pH adjusters, preservatives, binders, flavorings, whitening agents, foaming agents, or purified water, to ensure optimum formulation and formulation stability, increase a desired effect, and enhance usage preference.

The wetting agent includes, but is not limited to, for example, concentrated glycerin, glycerin, sorbitol or non-crystalline sorbitol, used alone or in combination, and may be present in an amount of 1 to 60 wt % based on the total weight of the oral composition, but is not limited thereto.

The abrasive includes, but is not limited to, for example, precipitated silica, silica gel, zirconium silicate, dibasic calcium phosphate, anhydrous dibasic calcium phosphate, hydrated alumina, calcium carbonate, light calcium carbonate, heavy calcium carbonate, calcium pyrophosphate, insoluble metaphosphate or aluminum silicate. Generally, the abrasive may be present in an amount of 1 to 60 wt % based on the total weight of the oral composition, but is not limited thereto.

The pharmaceutical agent includes, but is not limited to, for example, sodium fluoride, sodium monofluorophosphate, stannous fluoride, chlorhexidine, allantoin chlorohydroxyaluminate, aminocaproic acid, pyridoxine hydrochloride, tocopherol acetate, or enzymes, used alone or in combination.

In the present disclosure, the pharmaceutical agent is present in an amount of 0.005 to 5 wt % based on the total weight of the composition, i.e., 0.005, 0.01, 0.015, 0.02, 0.025, 0.03, 0.035, 0.4, 0.045, 0.05, 0.055, 0.06, 0.065, 0.07, 0.075, 0.08, 0.085, 0.09, 0.095, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5 wt %, preferably 0.01 to 2 wt %, and more preferably 0.3 to 1 wt %. Less than 0.005 wt % of the pharmaceutical agent fails to effectively produce its effect, and more than 5 wt % of the pharmaceutical agent fails to produce a notable effect compared to the content used.

The sweetening agent includes, but is not limited to, for example, sodium saccharin, xylitol, erythritol, or aspartame, and generally, the sweetening agent may be present in an amount of 0.05 to 0.5 wt % based on the total weight of the oral composition, but is not limited thereto.

The pH adjuster includes, but is not limited to, for example, sodium phosphate, disodium phosphate, citric acid, sodium citrate, sodium hydrogen carbonate, and the preferred pH of the composition according to the present disclosure is from 5 to 10.

The preservative includes, but is not limited to, for example, benzoic acid, methylparaben, propylparaben, para-hydroxybenzoate ester or sodium benzoate, used alone or in combination.

The binder includes, but is not limited to, for example, guar gum, pectin, carboxyvinylpolymer, sodium alginate, laponite, carbomer, carrageenan, xanthan gum, or alginates. Generally, the binder may be present in an amount of 0.1 to 3 wt % based on the total weight of the oral composition, and preferably 0.5 to 2 wt %, but is not limited thereto.

The flavoring includes, but is not limited to, for example, peppermint oil, spearmint oil, carvone or menthol, used alone or in combination, and preferably a flavoring mixture at a predetermined mix ratio may be mixed with anise oil in optimum amounts.

The whitening agent includes titanium oxide, and is preferably present in an amount of 0.1 to 2 wt %.

The foaming agent includes, but is not limited to, for example, an anionic surfactant such as sodium alkylsulfate and sodium lauryl sulfate, a non-ionic surfactant such as a copolymer (poloxamer) of polyoxyethylenepolyoxypropylene, polyoxyethylene hydrogenated castor oil, or polyoxyethylenesorbitan fatty acid ester. Generally, the foaming agent may be present in an amount of 0.5 to 5 wt % based on the total weight of the oral composition, and preferably 0.5 to 3.5 wt %, but is not limited thereto.

The sweetening agent includes, but is not limited to, for example, sodium saccharin, aspartame, and glycyrrhetinic acid, used alone or in combination, and may be present in an amount of 0.05 to 0.5 wt %.

The oral composition of the present disclosure may include other additive, for example, enzymes such as dextranase.

The oral composition of the present disclosure may include a remaining amount of water, preferably purified water, in addition to the active ingredients and the additives.

The oral composition according to the present disclosure may have formulations such as, for example, toothpastes, mouth washes, sprays, mouth rinses, gums, candies, solutions for mouth cleaning, and tooth whitening products, but is not limited thereto, and any formulation that can bring into contact with the oral tissues after introduction in the mouth is available without limitations, and the oral composition may be formulated by a general means known to those skilled in the art.

Further, the present disclosure provides a method for preventing or reducing tooth sensitivity symptoms, including applying a composition to a subject in need thereof, the composition containing i) a copper salt or a zinc salt; and ii) dicarboxylic acid or its salt as active ingredients.

The subject may be preferably a mammal, and more preferably a human, and preferably the applying refers to applying in the mouth.

An Oral Composition for Preventing or Reducing Tooth Sensitivity Containing i) Dicarboxylic Acid or its Salt; and ii) a Partially Soluble Calcium Salt as Active Ingredients In the present disclosure, to avoid the repeated disclosure, hereinafter the description of 'an oral composition for preventing or reducing tooth sensitivity containing i) dicarboxylic acid or its salt; and ii) a partially soluble calcium salt as active ingredients' is equally applied to 'a method for preventing or reducing tooth sensitivity symptoms including applying a composition containing i) dicarboxylic acid or its salt; and ii) a partially soluble calcium salt as active ingredients' and 'the use of i) dicarboxylic acid or its salt; and ii) a partially soluble calcium salt for preparing a composition for preventing or reducing tooth sensitivity symptoms'.

The inventors identified that as the composition of the present disclosure occludes the exposed dental tubules by forming a calcium complex with salvia and/or dental tubule fluid, the composition had a superior effect on the prevention and/or reduction of tooth sensitivity.

The dicarboxylic acid comes into contact with calcium ions in salvia to form a calcium complex, and when considering occlusion of dental tubules, reactivity with calcium ions and adhesion to teeth, preferably the dicarboxylic acid may be dicarboxylic acid having 2 to 9 carbon atoms, i.e., dicarboxylic acid having 2 carbon atoms, dicarboxylic acid having 3 carbon atoms, dicarboxylic acid having 4 carbon atoms, dicarboxylic acid having 5 carbon atoms, dicarboxylic acid having 6 carbon atoms, dicarboxylic acid having 7 carbon atoms, dicarboxylic acid having 8 carbon atoms, dicarboxylic acid having 9 carbon atoms. The calcium complex formed in the mouth can be easily introduced into the dental tubules, and when a partially soluble calcium salt, preferably a calcium salt having a solubility product constant ($K_{sp}$) of $10^{-5}$ to $10^{-20}$ is further included, a larger number of calcium complexes are formed, the dental tubules are occluded more effectively, and tooth sensitivity symptoms are prevented and/or reduced. Furthermore, preferably when phosphate is further included, a much better effect of the prevention and/or reduction of tooth sensitivity; and a tooth remineralization effect can be achieved, and this was identified by the inventors through experimentation.

That is, the composition is characterized by having tooth remineralization efficacy and/or dental tubule occlusion capability.

The present disclosure may include dicarboxylic acid or its salt, and preferably dicarboxylic acid or its salt having 2 to 9 carbon atoms.

The dicarboxylic acid includes, but is not limited to, for example, oxalic acid, malonic acid, succinic acid, glutaric acid, adipic acid, pimelic acid, suberic acid, azelaic acid or mixtures thereof, and preferably oxalic acid, malonic acid, succinic acid, glutaric acid, adipic acid or mixtures thereof that has higher water solubility when considering superior precipitate formation.

The salt of dicarboxylic acid refers to a combination of the dicarboxylic acid and a metal ion, and the metal includes, but is not limited to, for example, sodium (Na) and potassium (K).

In the present disclosure, the dicarboxylic acid or its salt is present in an amount of 0.01 to 5 wt % based on the total weight of the composition, i.e., 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5 wt %, preferably 0.1 to 3 wt %, and more preferably 0.1 to 1 wt %. Less than 0.01 wt % of the dicarboxylic acid or its salt is insufficient to generate a calcium complex and does not work on tooth sensitivity reduction, and more than 5 wt % of the dicarboxylic acid or its salt makes it impossible for practical use due to too strong taste of the raw material itself.

The composition of the present disclosure includes a partially soluble calcium salt to increase the occlusion effect of the dental tubules.

The term "partially soluble calcium salt" as used herein refers to a calcium salt that is partially, but not fully, dissolved in a solvent, preferably water, and preferably the partially soluble calcium salt used in the present disclosure is a calcium salt having a solubility product constant ($K_{sp}$) of $10^{-5}$ to $10^{-20}$. That is, the inventors identified that a calcium salt having too high solubility formed a calcium complex in products before it was applied to teeth due to a too fast reaction, and there was a remarkably superior effect with the addition of a calcium salt having optimum solubility to the composition of the present disclosure.

That is, the calcium salt includes calcium carbonate, calcium hydrogen phosphate, calcium sulphite, calcium sulfate, calcium fluoride, calcium hydroxide, calcium iodate or mixtures thereof.

Provided are examples of the calcium salt having a solubility product constant ($K_{sp}$) of $10^{-5}$ to $10^{-20}$ that can be added to the composition of the present disclosure, and the solubility product constant ($K_{sp}$) is as follows:

i) Calcium carbonate: $3.8 \times 10^{-9}$,
ii) Calcium hydrogen phosphate: $1 \times 10^{-7}$,
iii) Calcium sulphite: $6.8 \times 10^{-8}$,
iv) Calcium sulfate: $9.1 \times 10^{-6}$,
v) Calcium fluoride: $5.3 \times 10^{-9}$,
vi) Calcium hydroxide: $5.5 \times 10^{-6}$,
vii) Calcium iodate: $7.1 \times 10^{-7}$.

In the present disclosure, the calcium salt is present in an amount of 1 to 50 wt % based on the total weight of the composition, i.e., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 1 to 5, 5 to 10, 10 to 15, 15 to 20, 20 to 25, 25 to 30, 30 to 35, 35 to 40, 40 to 45, 45 to 50, 1 to 10, 10 to 20, 20 to 30, 30 to 40, 40 to 50 wt %, preferably 1 to 30 wt %, and more preferably 5 to 25 wt %. Less than 1 wt % of the calcium salt is insufficient to generate a calcium complex and does not work on tooth sensitivity reduction, and more than 50 wt % of the calcium salt yields excessive solids content, causing a problem with phase stability.

Further, in the present disclosure, a weight ratio of i) the dicarboxylic acid or its salt; and ii) the partially soluble calcium salt is 1:5~50 (dicarboxylic acid or its salt:partially soluble calcium salt), i.e., 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, preferably 1:10~40, and more preferably 1:15~35.

Preferably, the composition of the present disclosure may further include phosphate to increase the occlusion effect of the dental tubules. The inventors experimentally identified that there were remarkably superior effects on the tooth remineralization effect and the prevention and/or reduction of tooth sensitivity with the addition of phosphate to the composition of the present disclosure. That is, the inventors identified that further inclusion of phosphate produced the enhanced effect on the prevention and/or reduction of tooth sensitivity. Accordingly, most preferably the present disclosure provides an oral composition for preventing or reducing tooth sensitivity containing i) dicarboxylic acid or its salt; ii) a partially soluble calcium salt; and iii) phosphate as active ingredients.

In the present disclosure, the phosphate refers to a combination of phosphoric acid and a metal ion, and preferably the metal includes, but is not limited to, for example, sodium (Na) and potassium (K).

That is, the phosphate includes, but is not limited to, for example, monosodium phosphate, disodium phosphate, trisodium phosphate, monopotassium phosphate, dipotassium phosphate, tripotassium phosphate or mixtures thereof.

In the present disclosure, the phosphate is present in an amount of 0.01 to 10 wt % based on the total weight of the composition, i.e., 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10 wt %, preferably 0.1 to 7 wt %, and more preferably 0.5 to 5 wt %. Less than 0.01 wt % the phosphate does not work on tooth sensitivity reduction, and more than 10 wt % the phosphate reduces the solubility, causing a problem with phase stability.

Further, in the present disclosure, a weight ratio of i) the dicarboxylic acid or its salt; ii) the partially soluble calcium salt; and iii) the phosphate is 1:5~50:1~30 (dicarboxylic acid or its salt:partially soluble calcium salt:phosphate), i.e., 1:5:1~30, 1:10:1~30, 1:15:1~30, 1:20:1~30, 1:25:1~30, 1:30:1~30, 1:35:1~30, 1:40:1~30, 1:45:1~30, 1:50:1~30, 1:5~50:1, 1:5~50:2, 1:5~50:3, 1:5~50:4, 1:5~50:5, 1:5~50:6, 1:5~50:7, 1:5~50:8, 1:5~50:9, 1:5~50:10, 1:5~50:11, 1:5~50:12, 1:5~50:13, 1:5~50:14, 1:5~50:15, 1:5~50:16, 1:5~50:17, 1:5~50:18, 1:5~50:19, 1:5~50:20, 1:5~50:21, 1:5~50:22, 1:5~50:23, 1:5~50:24, 1:5~50:25, 1:5~50:26, 1:5~50:27, 1:5~50:28, 1:5~50:29, 1:5~50:30, preferably 1:10~40:2~25, and more preferably 1:15~35:2~20. The mixing at the weight ratio produces a synergetic effect on the prevention or reduction of tooth sensitivity symptoms, and the weight ratio out of the range has problems with formulation and product stability, and fails to obtain a desired effect on tooth sensitivity reduction.

The oral composition according to the present disclosure may further contain additives including, but is not limited to, for example, wetting agents, abrasives, pharmaceutical agent, sweetening agents, pH adjusters, preservatives, thickening agents, binders, flavorings, whitening agents, foaming agents, or purified water, to ensure optimum formulation and formulation stability, increase a desired effect, and enhance usage preference.

The wetting agent includes, but is not limited to, for example, concentrated glycerin, glycerin, sorbitol or non-crystalline sorbitol, used alone or in combination, and may be present in an amount of 1 to 60 wt % based on the total weight of the oral composition, but is not limited thereto.

The abrasive includes, but is not limited to, for example, silica (precipitated silica), silica gel, zirconium silicate, hydrated alumina, or aluminum silicate. Generally, the abrasive may be present in an amount of 1 to 60 wt % based on the total weight of the oral composition, but is not limited thereto.

The pharmaceutical agent includes, but is not limited to, for example, sodium fluoride, sodium monofluorophosphate, stannous fluoride, chlorohexidine, allantoin chlorohydroxyaluminate, aminocaproic acid, pyridoxine hydrochloride, tocopheryl acetate, tocopherol acetate, or enzymes, used alone or in combination.

In the present disclosure, the pharmaceutical agent may be present in an amount of 0.005 to 5 wt % based on the total weight of the composition, preferably 0.01 to 2 wt %, and more preferably 0.3 to 1 wt %. Less than 0.005 wt % of the pharmaceutical agent fails to effectively produce its effect, and more than 5 wt % of the pharmaceutical agent fails to produce a notable effect compared to the content used.

The sweetening agent includes, but is not limited to, for example, sodium saccharin, xylitol, erythritol, or aspartame, and generally the sweetening agent may be present in an amount of 0.05 to 0.5 wt % based on the total weight of the oral composition, but is not limited thereto.

The pH adjuster includes, but is not limited to, for example, citric acid, sodium citrate, and sodium hydrogen carbonate.

The preservative includes, but is not limited to, for example, benzoic acid, methylparaben, propylparaben, para-hydroxybenzoate ester or sodium benzoate, used alone or in combination.

The thickening agent includes, for example, carboxymethylcellulose.

The binder includes, but is not limited to, for example, guar gum, pectin, carboxyvinylpolymer, sodium alginate, laponite, carbomer, carrageenan, xanthan gum, or alginates. Generally, the binder may be present in an amount of 0.1 to 3 wt % based on the total weight of the oral composition, and more preferably 0.5 to 2 wt %, but is not limited thereto.

The flavoring includes, but is not limited to, for example, peppermint oil, spearmint oil, carvone or menthol, used alone or in combination, and preferably a flavoring mixture at a predetermined mix ratio may be mixed with anise oil in optimum amounts.

The whitening agent includes titanium oxide, and is preferably present in an amount of 0.1 to 2 wt %.

The foaming agent includes, but is not limited to, for example, an anionic surfactant such as sodium alkylsulfate and sodium lauryl sulfate, a non-ionic surfactant such as a copolymer (poloxamer) of polyoxyethylenepolyoxypropylene, polyoxyethylene hydrogenated castor oil, or polyoxyethylene sorbitan fatty acid ester. Generally, the foaming agent may be present in an amount of 0.5 to 5 wt % based on the total weight of the oral composition, and preferably 0.5 to 3.5 wt %, but is not limited thereto.

The sweetening agent includes, but is not limited to, for example, sodium saccharin, aspartame, and glycyrrhetinic acid, used alone or in combination, and may be present in an amount of 0.05 to 0.5 wt %.

The oral composition of the present disclosure may include other additive, for example, enzymes such as dextranase.

The oral composition of the present disclosure may include a remaining amount of water, preferably purified water, in addition to the active ingredients and the additives.

The oral composition according to the present disclosure may have formulations such as, for example, toothpastes, mouth washes, sprays, mouth rinses, gums, candies, solutions for mouth cleaning, and tooth whitening products, but is not limited thereto, and any formulation that can bring into contact with the oral tissues after introduction in the mouth is available without limitations, and the oral composition may be formulated by a general means known to those skilled in the art.

Advantageous Effects

Accordingly, the oral composition according to the present disclosure contains a copper salt or zinc salt which reacts with dental tubule fluid to form a protein complex to induce occlusion of dental tubules, and to maintain the occlusion effect of the dental tubules, includes a water soluble or alcohol soluble polymer to dramatically increase the occlusion effect of the dental tubules, producing an effect on the efficient prevention or reduction of tooth sensitivity symptoms in a short time.

Further, the oral composition according to the present disclosure includes a copper salt or a zinc salt which reacts with dental tubule fluid to form a protein complex, and includes dicarboxylic acid which reacts with an inorganic matter such as calcium to form a complex to induce occlusion of dental tubules and dramatically increase the occlusion effect, producing an effect on the efficient prevention or reduction of tooth sensitivity symptoms in a short time.

Further, the oral composition according to the present disclosure includes dicarboxylic acid and its salt which forms a calcium complex in the mouth to induce occlusion of dental tubules, and further includes a partially soluble calcium salt and/or phosphate to dramatically increase the occlusion effect of the dental tubules, producing an effect on the efficient prevention or reduction of tooth sensitivity symptoms in a short time.

Further, the present disclosure provides a method for preventing or reducing tooth sensitivity symptoms including applying a composition to a subject in need thereof, the composition containing i) dicarboxylic acid or its salt; and ii) a partially soluble calcium salt as active ingredients.

The subject may be preferably a mammal, and more preferably a human, and preferably the applying refers to applying in the mouth.

BEST MODE

Hereinafter, to describe the present disclosure in detail, a detailed description is provided through examples and experimental examples. However, examples and experimental examples according to the present disclosure may be modified in many different forms, and the scope of the present disclosure shall not be construed as being limited to the examples and experimental examples described below. The examples and experimental examples of the present disclosure are provided to help those skilled in the art understand the present disclosure more fully.

1. Composition Containing a Copper Salt or a Zinc Salt and/or a Water Soluble or Alcohol Soluble Polymer

Preparation of Examples 1 Through 9 and Comparative Examples 1 and 2

Toothpaste compositions of examples and comparative example were prepared according to the ingredients and composition ratios shown in the following Table 1. Sodium saccharin and preservative as powder components were dispersed in a sorbitol solution as a wetting agent, put in purified water and mixed in a mixer, and subsequently, precipitated silica or calcium carbonate as an abrasive, sodium monofluorophosphate as a pharmaceutical agent and a zinc salt or copper salt were fed and mixed. Finally, sodium lauryl sulfate as a foaming agent, water soluble or alcohol soluble polymers, stabilizers, and flavoring ingredients were put and mixed under the vacuum condition to prepare a toothpaste composition.

EXPERIMENTAL EXAMPLE 1-1

Protein Precipitation Effect Test in Dental Tubules

Using the toothpaste compositions of examples 1 and 2 and comparative examples 1 and 2 in Table 1, the protein precipitation effect of toothpaste was demonstrated using bovine serum proteins having similar components to dental tubule fluid.

1) Test Method
(1) Dental Tubule Fluid Precipitation Effect

A. After examples and comparative examples were fully dispersed in a saline solution at the concentration of 10% and were centrifugally separated, only a supernatant was put in an Eppendorf tube.

B. FBS was added so that a ratio of the FBS and the saline solution was 1:3 in the end.

C. The morphology of the precipitated protein was observed with an optical microscope and the results about precipitation ratios are shown in Table 2.

(2) Test Results

TABLE 2

| Test group | Precipitation ratio (%) |
|---|---|
| Example 1 | 8.24 ± 1.890 |
| Example 2 | 9.50 ± 2.02 |
| Comparative example 1 | 0 |
| Comparative example 2 | 0 |

Figure 1:
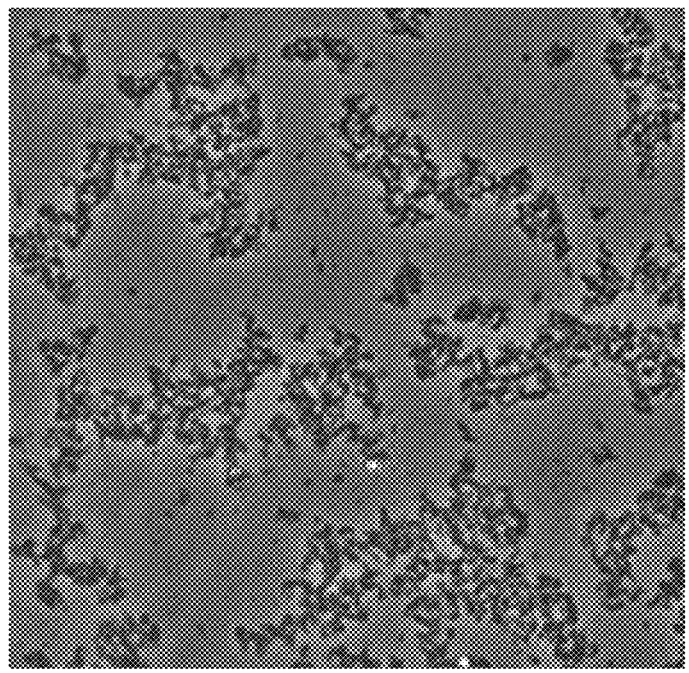
FIG. 1 is a photographic image showing protein precipitation of example 1.
Figure 2:
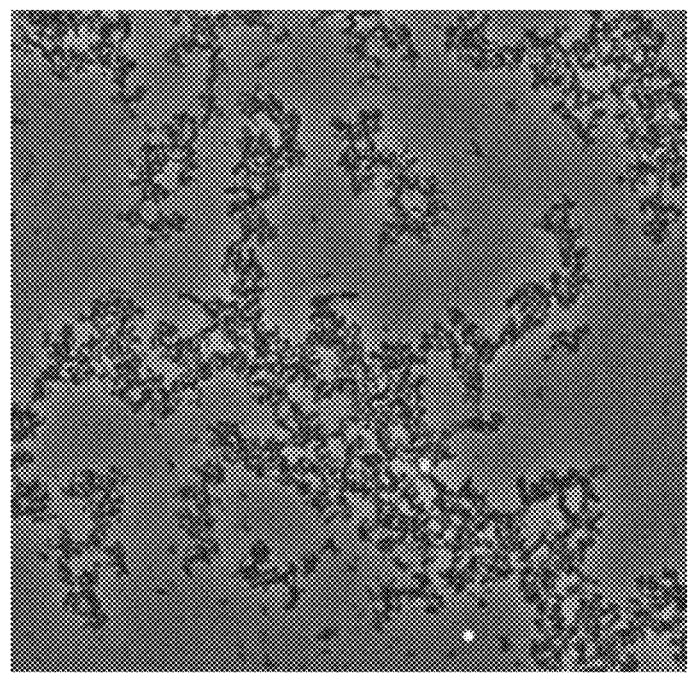
FIG. 2 is a photographic image showing protein precipitation of example 2.
Figure 3:
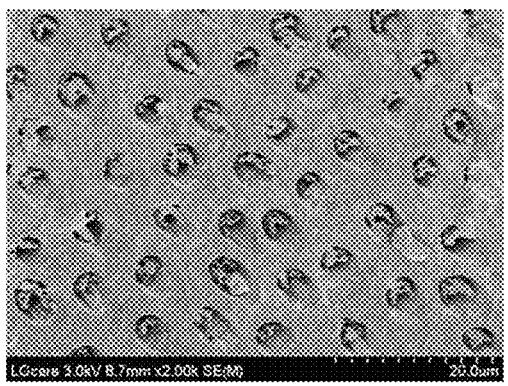
FIG. 3 is a photographic image showing results of examples 1 through 4 according to experimental example 1-2 (dental tubule occlusion capability).
Figure 3:
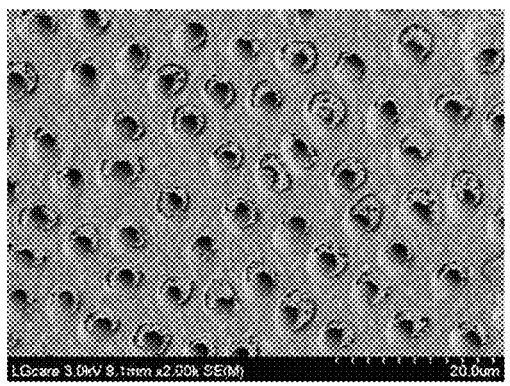
Figure 3:
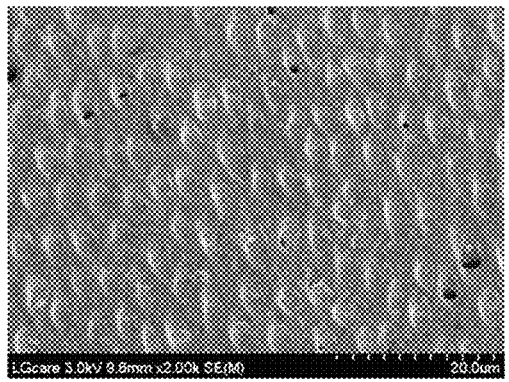
Figure 3:
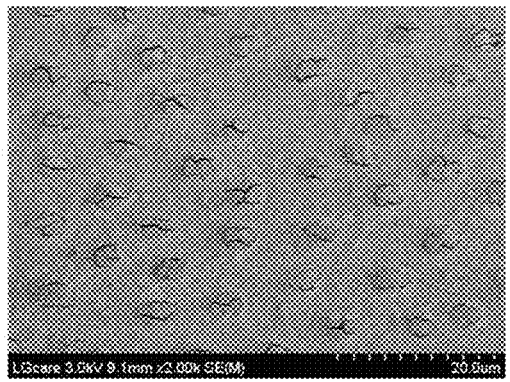
Figure 4:
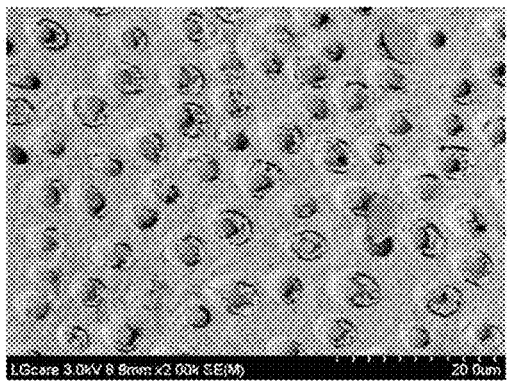
FIG. 4 is a photographic image showing results of examples 5 through 9 according to experimental example 1-2 (dental tubule occlusion capability).
Figure 4:
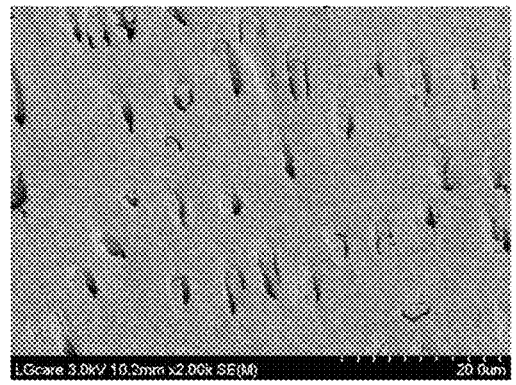
Figure 4:
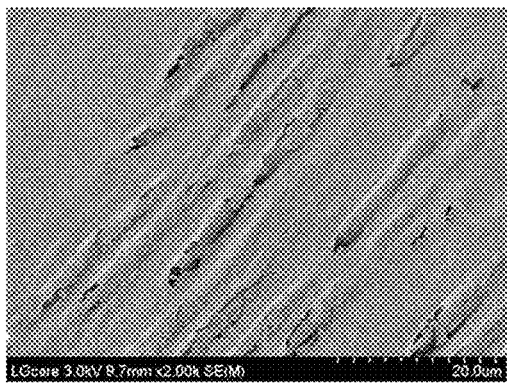
Figure 4:
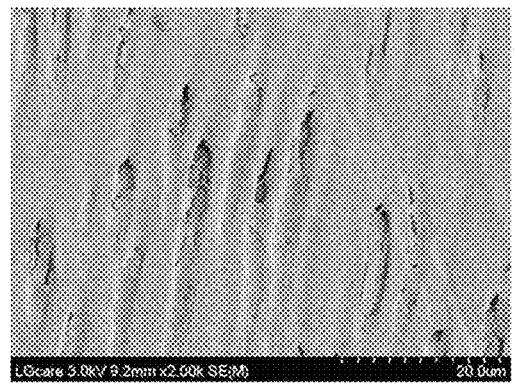
Figure 4:
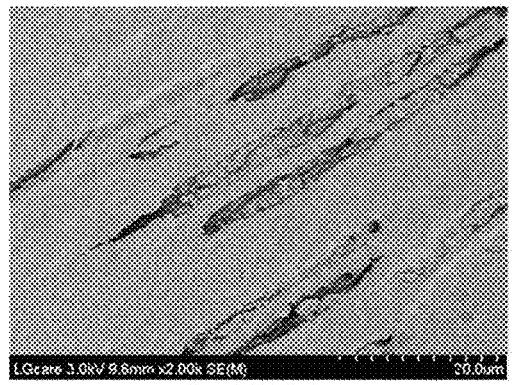
Figure 5:
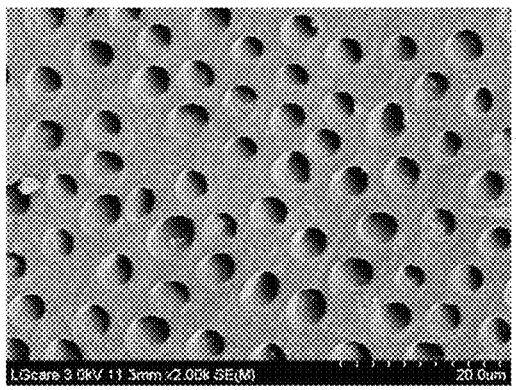
FIG. 5 is a photographic image showing results of comparative examples 1 and 2 according to experimental example 1-2 (dental tubule occlusion capability).
Figure 5:
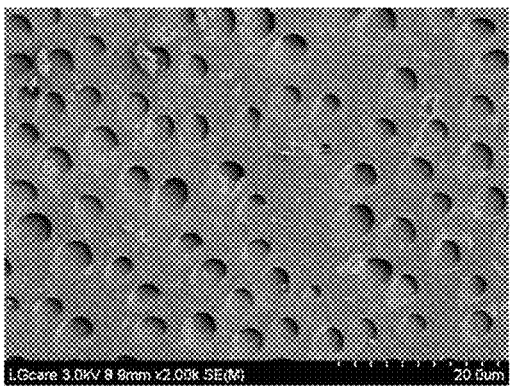

As can be seen from Table 2, examples 1 and 2 reacted with serum proteins to form a protein complex. Comparative examples 1 and 2 did not show any effect, while examples 1 and 2 formed a protein complex which had a size of about 2 μm and was found suitable to enter the dental tubules having a diameter of about 5 μm (FIGS. 1 and 2).

TABLE 1

| Unit (wt %) | Example 1 | Example 2 | Example 3 | Example 4 | Example 5 | Example 6 | Example 7 | Example 8 | Example 9 | Comparative example 1 | Comparative example 2 |
|---|---|---|---|---|---|---|---|---|---|---|---|
| Precipitated silica | 10.00 | 10.00 | 10.00 | 10.00 | 10.00 | 10.00 | 10.00 | — | — | 10.00 | — |
| Calcium carbonate | 10.00 | 10.00 | 10.00 | 10.00 | 10.00 | 10.00 | 10.00 | 38.00 | 38.00 | 10.00 | 38.00 |
| Sorbitol | 30.00 | 30.00 | 30.00 | 30.00 | 30.00 | 30.00 | 30.00 | 30.00 | 30.00 | 30.00 | 30.00 |
| Sodium lauryl sulfate | 2.00 | 2.00 | 2.00 | 2.00 | 2.00 | 2.00 | 2.00 | 2.00 | 2.00 | 2.00 | 2.00 |
| Sodium saccharin | 0.10 | 0.10 | 0.10 | 0.10 | 0.10 | 0.10 | 0.10 | 0.10 | 0.10 | 0.10 | 0.10 |
| Para-hydroxybenzoate ester | 0.10 | 0.10 | 0.10 | 0.10 | 0.10 | 0.10 | 0.10 | 0.10 | 0.10 | 0.10 | 0.10 |
| sodium monofluoro-phosphate | 0.76 | 0.76 | 0.76 | 0.76 | 0.76 | 0.76 | 0.76 | 0.76 | 0.76 | 0.76 | 0.76 |
| Copper chlorophyllin | 0.09 | — | — | — | — | 0.09 | 0.09 | — | — | — | — |
| Zinc chloride | — | 0.09 | — | — | — | — | — | 0.09 | 0.09 | — | — |
| Polyethyleneglycol | — | — | 1.0 | — | — | 1.0 | — | 1.0 | — | — | — |
| Hydroxypropyl methylcellulose | — | — | — | 1.0 | — | — | 1.0 | — | 1.0 | — | — |
| Methylcellulose | — | — | — | — | 1.0 | — | — | — | — | — | — |
| Purified water | up to 100.0 | up to 100.0 | up to 100.0 | up to 100.0 | up to 100.0 | up to 100.0 | up to 100.0 | up to 100.0 | up to 100.0 | up to 100.0 | up to 100.0 |

EXPERIMENTAL EXAMPLE 1-2

Dental Tubule Occlusion Capability (Dentin Coverage Evaluation)

For the dental tubule occlusion effect of toothpaste using the toothpaste compositions of examples 1 through 9 and comparative examples 1 and 2 in Table 1, its results was seen in an SEM Image by a dental tubule occlusion capability evaluation method using bovine tooth sample.

2) Test Method (1) Dental Tubule Occlusion Capability

A. After the bovine tooth sample was surface-ground to expose dental tubules and was surface-decalcified using a citric acid solution, the sample was treated with the toothpastes of examples and comparative examples and artificial saliva 20 times repeatedly.

B. The treated sample was washed with distilled water, dried, and observed from an SEM Image. The SEM Image results were evaluated using 6 point scale as below, 3 points or more were determined to be effective, and its results are shown in Table 3.

Evaluation Criteria

6: Fully cover the surface and form a multi-layer.

5: Occlude dental tubules and fully cover the dentin surface.

4: Penetrate into dental tubules, and cover parts of the surface.

3: 50% or more of dental tubules and dentin surface was covered.

2: Precipitate was observed on dental tubules and dentin surface and 50% or less was covered.

1: Fail to occlude dental tubules.

2) Test Results

TABLE 3

| Test toothpaste group | Evaluation of dental tubule occlusion capability |
|---|---|
| Example 1 | 3 |
| Example 2 | 3 |
| Example 3 | 5 |
| Example 4 | 5 |
| Example 5 | 4 |
| Example 6 | 6 |
| Example 7 | 6 |
| Example 8 | 6 |
| Example 9 | 6 |
| Comparative example 1 | 1 |
| Comparative example 2 | 1 |

As can be seen from Table 3, it was found that comparative examples 1 and 2 did not occlude dental tubules, while examples 1 and 2 inducing protein precipitation had a dental tubule occlusion capability, and examples 3 through 5 containing a water soluble or alcohol soluble polymer were uniformly coated on the dentin surface and had superior dental tubule occlusion efficiency when compared to comparative examples 1 and 2 with no water soluble or alcohol soluble polymer. It was found that examples 6 through 9 containing both a protein precipitation derivative and a water soluble or alcohol soluble polymer formed a much thicker layer than examples 3 through 5 covering the dental tubules surface, showed the highest dental tubules occlusion ratio, and had increased occlusion retention efficiency, achieving efficient tooth sensitivity reductions through a synergistic effect of the two.

2. Composition Containing a Copper Salt or a Zinc Salt; and Dicarboxylic Acid or its Salt Preparation of Examples 10 Through 15 and Comparative Examples 3 Through 9

Toothpaste compositions of examples and comparative example were prepared according to the ingredients and composition ratios shown in the following Table 4. More specifically, sodium saccharin and preservative (para-hydroxybenzoate ester) as powder components were dispersed in a sorbitol solution as a wetting agent, put in purified water and mixed in a mixer, and subsequently, precipitated silica or calcium carbonate as an abrasive, sodium monofluorophosphate as a pharmaceutical agent, a zinc salt or a copper salt and dicarboxylic acid or its salt were fed and mixed. Finally, sodium lauryl sulfate as a foaming agent was put and mixed under the vacuum condition to prepare a toothpaste composition.

TABLE 4

| Unit (wt %) | Example 10 | Example 11 | Example 12 | Example 13 | Example 14 | Example 15 | Comparative example 3 |
|---|---|---|---|---|---|---|---|
| Precipitated silica | 10.00 | 10.00 | 10.00 | 10.00 | 10.00 | 10.00 | 10.00 |
| Calcium carbonate | 10.00 | 10.00 | 10.00 | 10.00 | 10.00 | 10.00 | 10.00 |
| Sorbitol | 30.00 | 30.00 | 30.00 | 30.00 | 30.00 | 30.00 | 30.00 |
| Sodium lauryl sulfate | 2.00 | 2.00 | 2.00 | 2.00 | 2.00 | 2.00 | 2.00 |
| Sodium saccharin | 0.10 | 0.10 | 0.10 | 0.10 | 0.10 | 0.10 | 0.10 |
| Para-hydroxybenzoate ester | 0.10 | 0.10 | 0.10 | 0.10 | 0.10 | 0.10 | 0.10 |
| Sodium monofluorophosphate | 0.76 | 0.76 | 0.76 | 0.76 | 0.76 | 0.76 | 0.76 |
| Copper chlorophyllin | 0.09 | 0.09 | — | — | — | — | — |
| Zinc chloride | — | — | 0.09 | 0.09 | 0.09 | 0.09 | — |
| Oxalic acid | — | — | 0.5 | — | — | — | — |
| Succinic acid | — | — | — | 0.5 | — | — | — |
| Sodium succinate | 0.5 | — | — | — | 0.5 | — | — |

TABLE 4-continued

| Unit (wt %) | Comparative example 4 | Comparative example 5 | Comparative example 6 | Comparative example 7 | Comparative example 8 | Comparative example 9 |
|---|---|---|---|---|---|---|
| Adipic acid | — | 0.5 | — | — | — | 0.5 | — |
| Purified water | To 100.0 | To 100.0 | To 100.0 | To 100.0 | To 100.0 | To 100.0 | To 100.0 |

| Unit (wt %) | Comparative example 4 | Comparative example 5 | Comparative example 6 | Comparative example 7 | Comparative example 8 | Comparative example 9 |
|---|---|---|---|---|---|---|
| Precipitated silica | 10.00 | 10.00 | 10.00 | 10.00 | 10.00 | 10.00 |
| Calcium carbonate | 10.00 | 10.00 | 10.00 | 10.00 | 10.00 | 10.00 |
| Sorbitol | 30.00 | 30.00 | 30.00 | 30.00 | 30.00 | 30.00 |
| Sodium lauryl sulfate | 2.00 | 2.00 | 2.00 | 2.00 | 2.00 | 2.00 |
| Sodium saccharin | 0.10 | 0.10 | 0.10 | 0.10 | 0.10 | 0.10 |
| Para-hydroxybenzoate ester | 0.10 | 0.10 | 0.10 | 0.10 | 0.10 | 0.10 |
| Sodium monofluoro-phosphate | 0.76 | 0.76 | 0.76 | 0.76 | 0.76 | 0.76 |
| Copper chlorophyllin | 0.09 | — | — | — | — | — |
| Zinc chloride | — | 0.09 | — | — | — | — |
| Oxalic acid | — | — | 0.5 | — | — | — |
| Succinic acid | — | — | — | 0.5 | — | — |
| Sodium succinate | — | — | — | — | 0.5 | — |
| Adipic acid | — | — | — | — | — | 0.5 |
| Purified water | To 100.0 | To 100.0 | To 100.0 | To 100.0 | To 100.0 | To 100.0 |

EXPERIMENTAL EXAMPLE 2-1

Dental Tubule Occlusion Capability (Dentin Coverage Evaluation)

For the dental tubule occlusion effect of toothpaste using the toothpaste compositions of examples 10 through 15 and comparative examples 3 through 9 in Table 4, its results were seen in an SEM Image by a dental tubule occlusion capability evaluation method using bovine tooth sample.
1) Test Method
The test method and evaluation criteria are the same as experimental example 1-2.
2) Test Results
The test results are shown in the following Table 5.

TABLE 5

| Test toothpaste group | Evaluation of dental tubule occlusion capability |
|---|---|
| Example 10 | 6 |
| Example 11 | 6 |
| Example 12 | 5 |
| Example 13 | 6 |
| Example 14 | 6 |
| Example 15 | 6 |
| Comparative example 3 | 1 |
| Comparative example 4 | 3 |
| Comparative example 5 | 3 |
| Comparative example 6 | 2 |
| Comparative example 7 | 3 |
| Comparative example 8 | 3 |
| Comparative example 9 | 3 |

Figure 6:
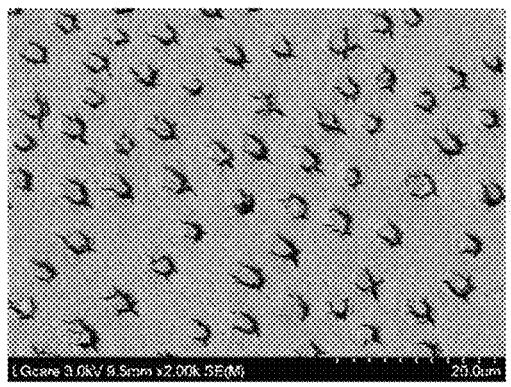
FIG. 6 is a photographic image showing results of examples 10 through 15 according to experimental example 2-1 (dental tubule occlusion capability).
Figure 6:
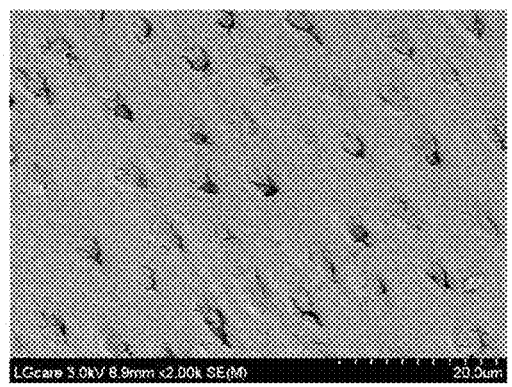
Figure 6:
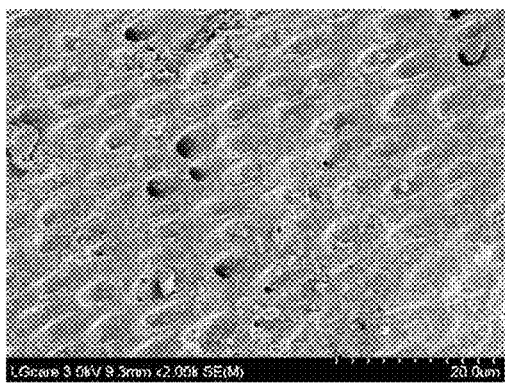
Figure 6:
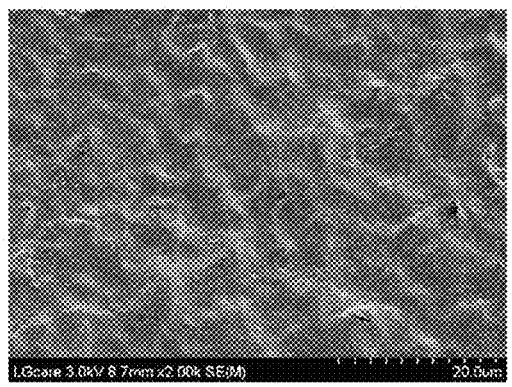
Figure 6:
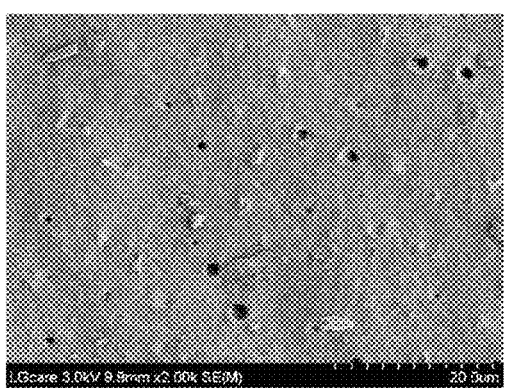
Figure 6:
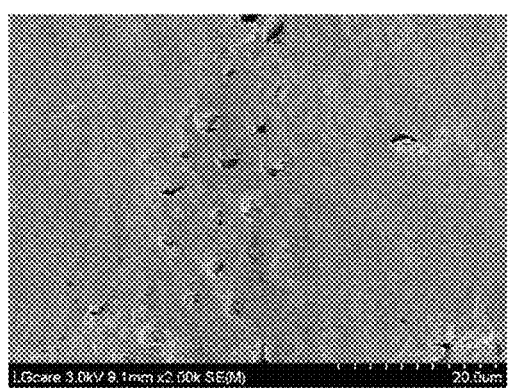
Figure 7:
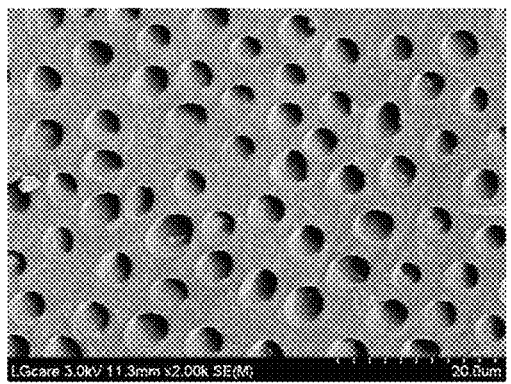
FIG. 7 is a photographic image showing results of comparative example 3 through 6 according to experimental example 2-1 (dental tubule occlusion capability).
Figure 7:
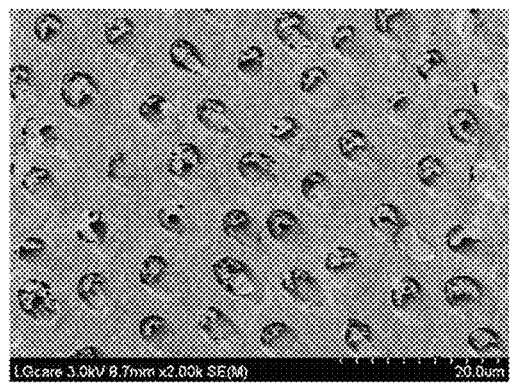
Figure 7:
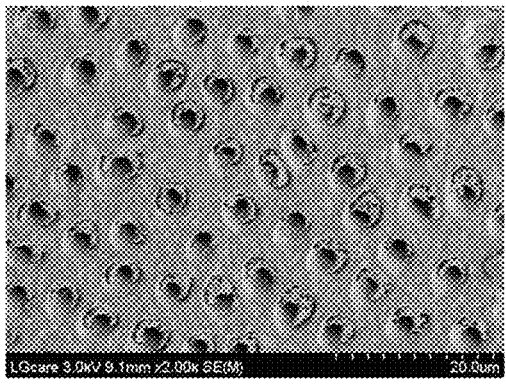
Figure 7:
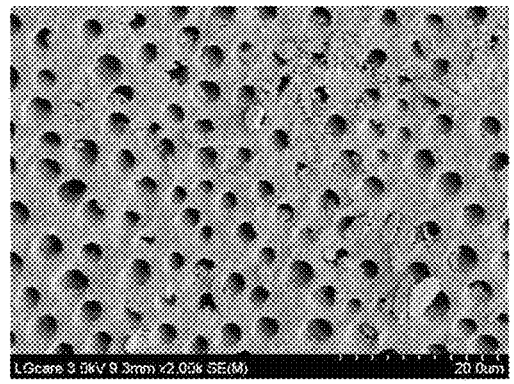
Figure 8:
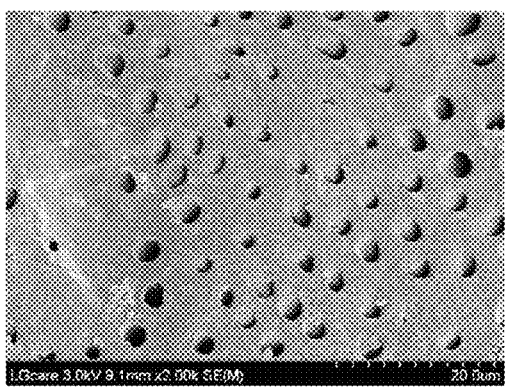
FIG. 8 is a photographic image showing results of comparative examples 7 through 9 according to experimental example 2-1 (dental tubule occlusion capability).
Figure 8:
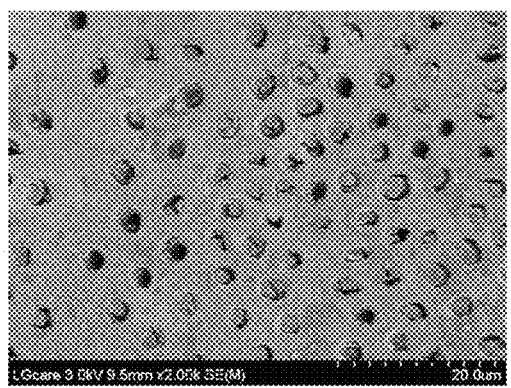
Figure 8:
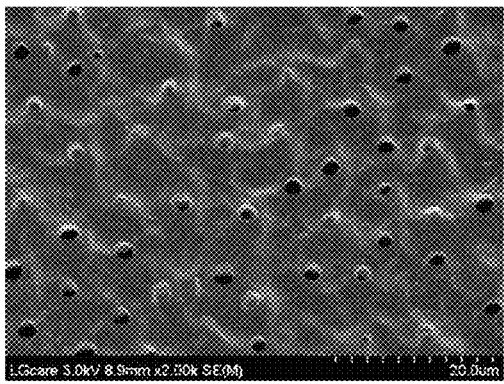
Figure 9:
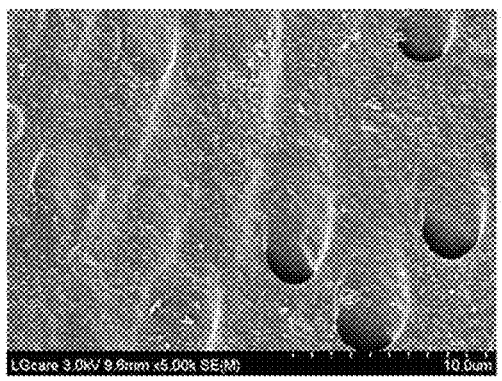
FIG. 9 is a photographic image showing results of examples 16 through 21 according to experimental example 3-2 (dental tubule occlusion capability).
Figure 9:
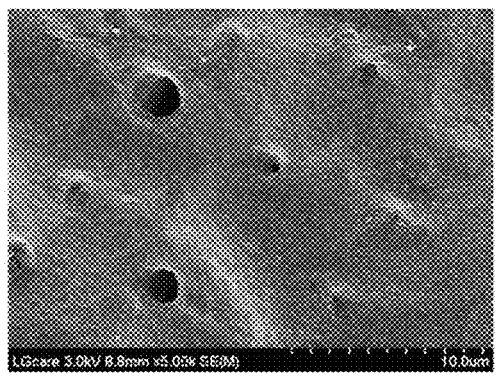
Figure 9:
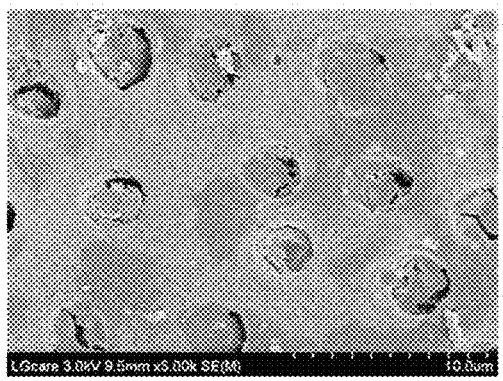
Figure 9:
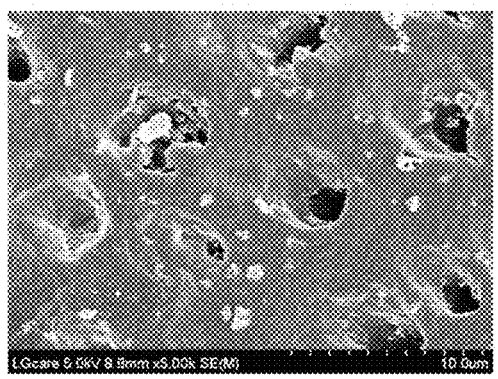
Figure 9:
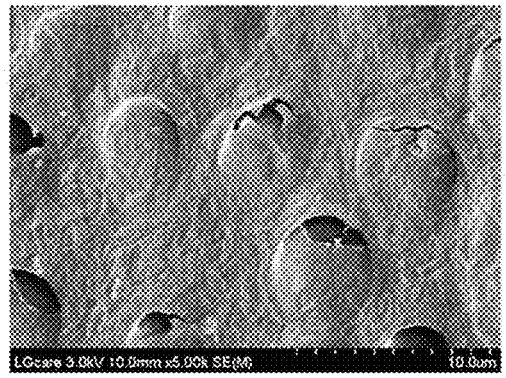
Figure 9:
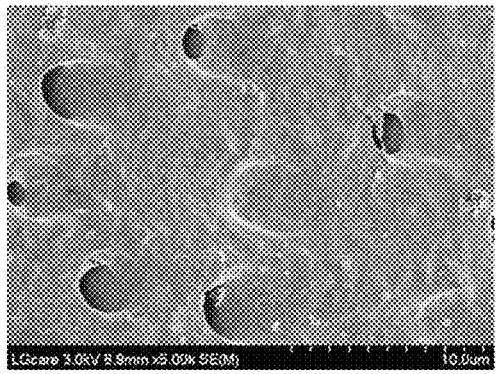
Figure 10:
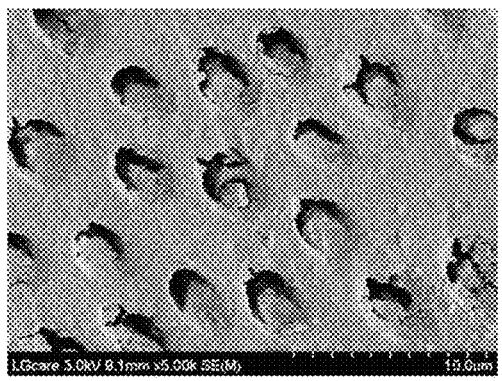
FIG. 10 is a photographic image showing results of examples 23 through 27 according to experimental example 3-2 (dental tubule occlusion capability).
Figure 10:
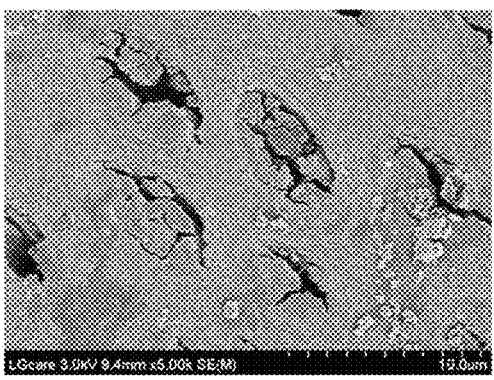
Figure 10:
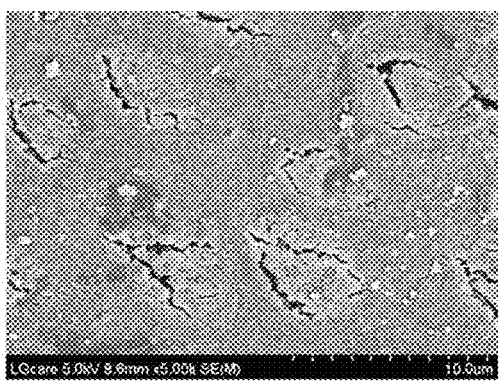
Figure 10:
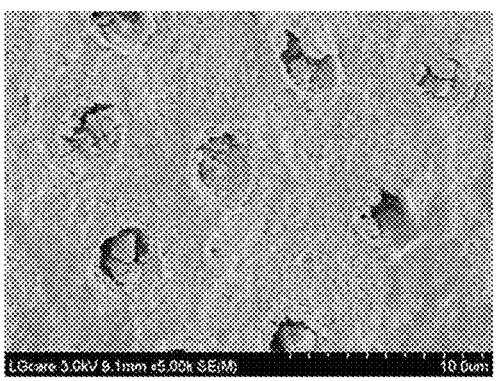
Figure 10:
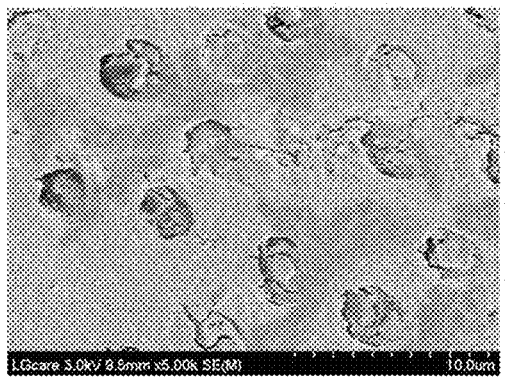
Figure 11:
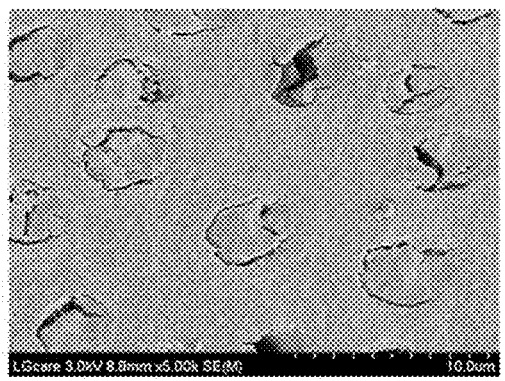
FIG. 11 is a photographic image showing results of examples 28 through 32 according to experimental example 3-2 (dental tubule occlusion capability).
Figure 11:
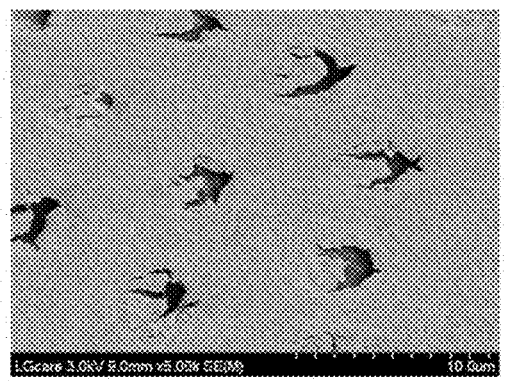
Figure 11:
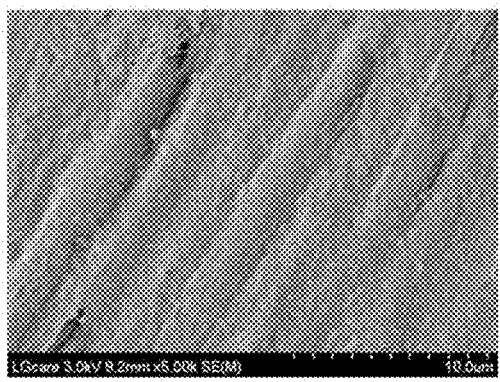
Figure 11:
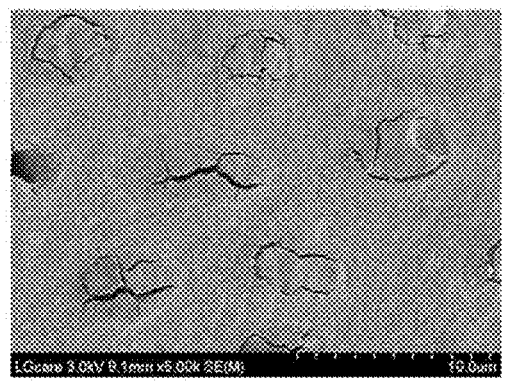
Figure 11:
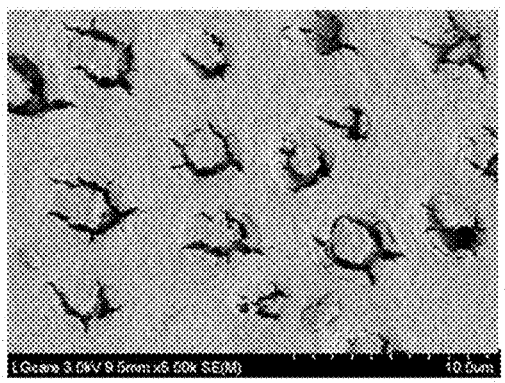
Figure 12:
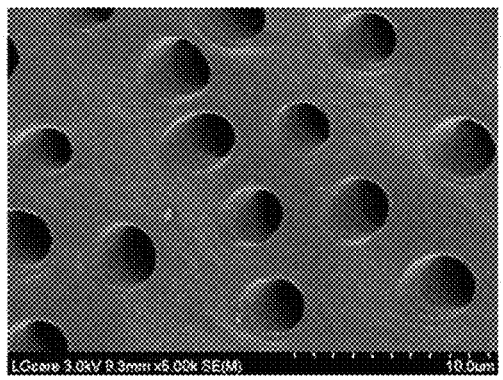
FIG. 12 is a photographic image showing results of comparative examples 10 through 15 according to experimental example 3-2 (dental tubule occlusion capability).
Figure 12:
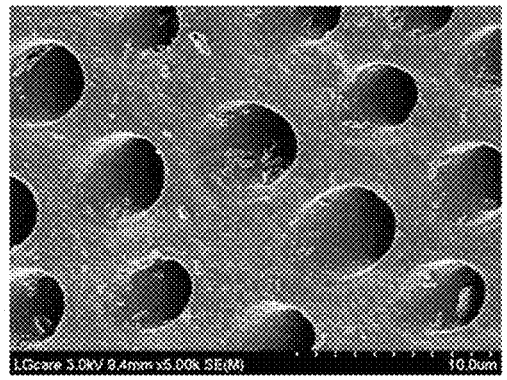
Figure 12:
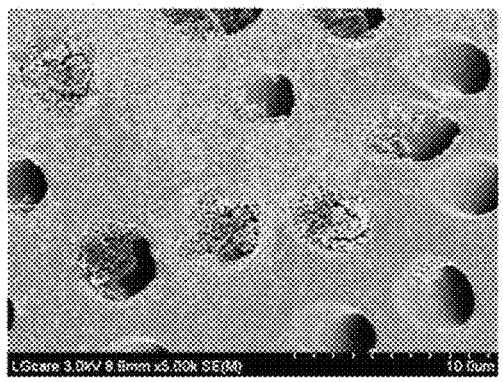
Figure 12:
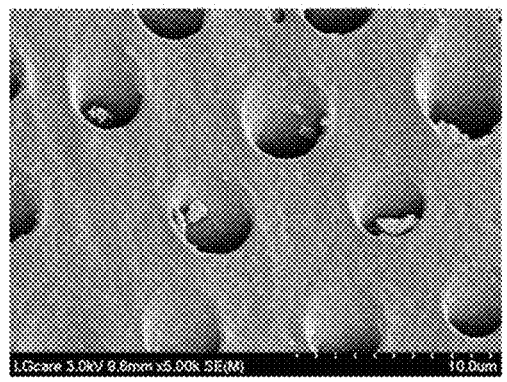
Figure 12:
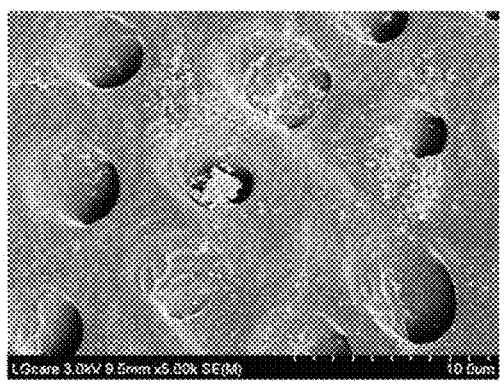
Figure 12:
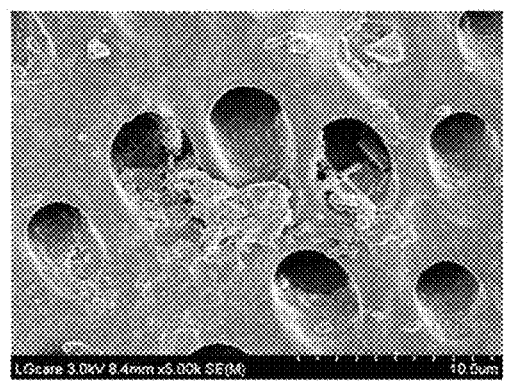

As can be seen from FIGS. 6 through 8 and Table 5, comparative example 3 with no tooth sensitivity reducing preparation had no dental tubule occlusion effect, and when a copper salt or zinc salt (comparative examples 4, 5) that reacts with an organic matter to form a precipitate is used alone, and when dicarboxylic acid (comparative examples 6, 7, 8, 9) that reacts with an inorganic matter such as calcium to form a precipitate is used alone, the dental tubule occlusion effect tends to slightly reduce. However, it was found that when a copper salt or zinc salt and dicarboxylic acid or its salt were used together (examples 10 through 15), the two substances reacted with both an organic matter and an inorganic matter to form a precipitate, an amount of the water insoluble precipitates generated by the reaction increased, and attachment to teeth was good, enhancing the tooth sensitivity reduction effect. Particularly, in the case of oxalic acid, when used alone, its effect is low, but when used with an organic complex such as a copper salt or a zinc salt, the effect dramatically increased, and it was found that efficient tooth sensitivity reductions were achieved through a synergistic effect of the two (example 12, comparative example 6).

3. Composition Containing Dicarboxylic Acid or its Salt; and a Partially Soluble Calcium Salt Preparation of Examples 16 Through 23 and Comparative Examples 10 Through 12

Toothpaste compositions of examples and comparative example were prepared according to the ingredients and composition ratios shown in the following Table 6. Powder components, dicarboxylic acid or its salt and sodium monofluorophosphate as a pharmaceutical agent, were dispersed in a sorbitol solution as a wetting agent, put in purified water and mixed in a mixer, and subsequently, silica (precipitated silica) as an abrasive, a calcium salt having a solubility product constant ($K_{sp}$) of $10^{-5}$ to $10^{-20}$ such as calcium carbonate and calcium hydrogen phosphate, carboxymethylcellulose as a thickening agent, and xanthan gum were fed and mixed. Sodium lauryl sulfate as a foaming agent, and finally tocopheryl acetate as a pharmaceutical agent were put and mixed under the vacuum condition to prepare a toothpaste composition.

TABLE 6

|  | Ingredient name | Example 16 | 17 | 18 | 19 | 20 | 21 | 22 | 23 | Comparative example 10 | 11 | 12 |
|---|---|---|---|---|---|---|---|---|---|---|---|---|
|  | Silica | 10.00 | 10.00 | 10.00 | 10.00 | 10.00 | 10.00 | 10.00 | 10.00 | 10.00 | 10.00 | 10.00 |
|  | Carboxymethylcellulose | 1.50 | 1.50 | 1.50 | 1.50 | 1.50 | 1.50 | 1.50 | 1.50 | 1.50 | 1.50 | 1.50 |
|  | Xanthan gum | 0.50 | 0.50 | 0.50 | 0.50 | 0.50 | 0.50 | 0.50 | 0.50 | 0.50 | 0.50 | 0.50 |
|  | Sodium monofluorophosphate | 0.76 | 0.76 | 0.76 | 0.76 | 0.76 | 0.76 | 0.76 | 0.76 | 0.76 | 0.76 | 0.76 |
|  | Tocopheryl acetate | 0.10 | 0.10 | 0.10 | 0.10 | 0.10 | 0.10 | 0.10 | 0.10 | 0.10 | 0.10 | 0.10 |
|  | Sodium lauryl sulfate | 2.00 | 2.00 | 2.00 | 2.00 | 2.00 | 2.00 | 2.00 | 2.00 | 2.00 | 2.00 | 2.00 |
|  | Sorbitol | 50.00 | 50.00 | 50.00 | 50.00 | 50.00 | 50.00 | 50.00 | 50.00 | 50.00 | 50.00 | 50.00 |
| Dicarboxylic acid and its salt | Succinic acid | 0.50 | 0.50 | 0.50 | 0.50 | — | — | — | — | — | 0.50 | 0.50 |
|  | Adipic acid | — | — | — | — | 0.50 | — | — | — | — | — | — |
|  | Sodium succinate | — | — | — | — | — | 0.50 | — | — | — | — | — |
|  | Sodium adipate | — | — | — | — | — | — | 0.50 | — | — | — | — |
|  | Oxalic acid | — | — | — | — | — | — | — | 0.50 | — | — | — |
| Calcium salt | Calcium carbonate | 10.00 | — | — | — | 10.00 | 10.00 | 10.00 | 10.00 | 10.00 | — | — |
|  | Calcium hydrogen phosphate | — | 10.00 | — | — | — | — | — | — | — | — | — |
|  | Calcium sulphite | — | — | 10.00 | — | — | — | — | — | — | — | — |
|  | Calcium sulfate | — | — | — | 10.00 | — | — | — | — | — | — | — |
|  | Calcium chloride | — | — | — | — | — | — | — | — | — | — | 10.00 |
|  | Purified water | To 100 | To 100 | To 100 | To 100 | To 100 | To 100 | To 100 | To 100 | To 100 | To 100 | To 100 |

Preparation of Examples 24 Through 32 and Comparative Examples 13 Through 15

Toothpaste compositions of examples and comparative example were prepared according to the ingredients and composition ratios shown in the following Table 7. Powder components, dicarboxylic acid or its salt, sodium monofluorophosphate as a pharmaceutical agent, and phosphate such as potassium phosphate and sodium phosphate, were dispersed in a sorbitol solution as a wetting agent, put in purified water and mixed in a mixer, and subsequently, silica (precipitated silica) as an abrasive, a calcium salt having a solubility product constant ($K_{sp}$) of $10^{-5}$ to $10^{-20}$ such as calcium carbonate and calcium hydrogen phosphate, carboxymethylcellulose as a thickening agent, and xanthan gum were fed and mixed. Sodium lauryl sulfate as a foaming agent, and finally tocopheryl acetate as a pharmaceutical agent were put and mixed under the vacuum condition to prepare a toothpaste composition.

TABLE 7

|  | Ingredient name | Example 24 | 25 | 26 | 27 | 28 | 29 | 30 | 31 | 32 | Comparative example 13 | 14 | 15 |
|---|---|---|---|---|---|---|---|---|---|---|---|---|---|
|  | Silica | 10.00 | 10.00 | 10.00 | 10.00 | 10.00 | 10.00 | 10.00 | 10.00 | 10.00 | 10.00 | 10.00 | 10.00 |
|  | Carboxymethylcellulose | 1.50 | 1.50 | 1.50 | 1.50 | 1.50 | 1.50 | 1.50 | 1.50 | 1.50 | 1.50 | 1.50 | 1.50 |
|  | Xanthan gum | 0.50 | 0.50 | 0.50 | 0.50 | 0.50 | 0.50 | 0.50 | 0.50 | 0.50 | 0.50 | 0.50 | 0.50 |
|  | Sodium monofluorophosphate | 0.76 | 0.76 | 0.76 | 0.76 | 0.76 | 0.76 | 0.76 | 0.76 | 0.76 | 0.76 | 0.76 | 0.76 |
|  | Tocopheryl acetate | 0.10 | 0.10 | 0.10 | 0.10 | 0.10 | 0.10 | 0.10 | 0.10 | 0.10 | 0.10 | 0.10 | 0.10 |
|  | Sodium lauryl sulfate | 2.00 | 2.00 | 2.00 | 2.00 | 2.00 | 2.00 | 2.00 | 2.00 | 2.00 | 2.00 | 2.00 | 2.00 |
|  | Sorbitol | 50.00 | 50.00 | 50.00 | 50.00 | 50.00 | 50.00 | 50.00 | 50.00 | 50.00 | 50.00 | 50.00 | 50.00 |
| Dicarboxylic acid and its salt | Succinic acid | 0.50 | 0.50 | 0.50 | 0.50 | 0.50 | — | — | — | — | — | 0.50 | 0.50 |
|  | Adipic acid | — | — | — | — | — | 0.50 | — | — | — | — | — | — |
|  | Sodium succinate | — | — | — | — | — | — | 0.50 | — | — | — | — | — |
|  | Sodium adipate | — | — | — | — | — | — | — | 0.50 | — | — | — | — |
|  | Oxalic acid | — | — | — | — | — | — | — | — | 0.50 | — | — | — |
| Calcium salt | Calcium carbonate | 10.00 | — | — | — | 10.00 | 10.00 | 10.00 | 10.00 | 10.00 | 10.00 | — | — |
|  | Calcium hydrogen phosphate | — | 10.00 | — | — | — | — | — | — | — | — | — | — |
|  | Calcium sulphite | — | — | 10.00 | — | — | — | — | — | — | — | — | — |
|  | Calcium sulfate | — | — | — | 10.00 | — | — | — | — | — | — | — | — |
|  | Calcium chloride | — | — | — | — | — | — | — | — | — | — | — | 10.00 |
| Phosphate | Potassium phosphate | 2.00 | 2.00 | 2.00 | 2.00 | — | 2.00 | 2.00 | 2.00 | 2.00 | 2.00 | 2.00 | 2.00 |
|  | Sodium phosphate | — | — | — | — | 2.00 | — | — | — | — | — | — | — |
|  | Purified water | To 100 | To 100 | To 100 | To 100 | To 100 | To 100 | To 100 | To 100 | To 100 | To 100 | To 100 | To 100 |

EXPERIMENTAL EXAMPLE 3-1

Investigation of Remineralization Effect

The inventors measured the remineralization effect of toothpaste composition using the toothpaste compositions of examples 16 through 32 and comparative examples 10 through 15 in Tables 6 and 7.

1) Test Method
(1) Tooth Remineralization Test

A. After the bovine tooth sample was surface-ground to expose dental tubules and was surface-decalcified using a citric acid solution, the sample was treated with the toothpastes of examples and comparative examples and artificial saliva 20 times repeatedly according to the ADA's tooth decay prevention test method.

B. After the initial hardness and the final hardness were measured using a Vickers hardness tester, the degree of remineralization was measured using a change value (ΔVHN, Vickers hardness number).

2) Test Results

The test results are shown in the following Table 8.

TABLE 8

| Sample name | | ΔVHN |
|---|---|---|
| Example | 16 | 22.5 |
| | 17 | 23.5 |
| | 18 | 22.8 |
| | 19 | 22.9 |
| | 20 | 19.8 |
| | 21 | 22.5 |
| | 22 | 23.8 |
| | 23 | 25.5 |
| | 24 | 35.5 |
| | 25 | 36.8 |
| | 26 | 37.8 |
| | 27 | 35.9 |
| | 28 | 33.6 |
| | 29 | 35.9 |
| | 30 | 37.5 |
| | 31 | 36.8 |
| | 32 | 35.7 |
| Comparative example | 10 | 8.3 |
| | 11 | 10.6 |
| | 12 | 12.5 |
| | 13 | 13.5 |
| | 14 | 13.8 |
| | 15 | 8.5 |

As can be seen from Table 8, it was found that examples 16 through 23 had an increase in tooth hardness by a calcium salt having a solubility product constant ($K_{sp}$) of $10^{-5}$ to $10^{-20}$ and dicarboxylic acid or its salt when compared to comparative examples 10 through 15. Further, it was found that a hardness increase rate of examples 24 through 32 further increased in hardness increase width by a synergetic effect of a calcium salt having a solubility product constant ($K_{sp}$) of $10^{-5}$ to $10^{-20}$, dicarboxylic acid or its salt and phosphate. However, in the case of comparative examples 12 and 15 with a salt having high solubility, a calcium salt reacted with dicarboxylic acid and phosphate immediately, influencing on tooth remineralization negatively rather than positively.

EXPERIMENTAL EXAMPLE 3-2

Dental Tubule Occlusion Capability (Dentin Coverage Evaluation)

After the toothpaste compositions of examples 16 through 32 and comparative examples 10 through 15 in Table 6 and 7 were dispersed in artificial saliva at 1:3, the dental tubule occlusion effect of toothpaste was imaged using a scanning electronic microscope, and then, the results were seen in the SEM Image using a dental tubule occlusion capability evaluation method.

1) Test Method

The test method and evaluation criteria are the same as experimental example 1-2.

2) Test Results

The test results are shown in the following Table 9.

TABLE 9

| Sample name | | Occlusion capability |
|---|---|---|
| Example | 16 | 4 |
| | 17 | 4 |
| | 18 | 4 |
| | 19 | 4 |
| | 20 | 4 |
| | 21 | 4 |
| | 22 | 4 |
| | 23 | 3 |
| | 24 | 6 |
| | 25 | 6 |
| | 26 | 6 |
| | 27 | 6 |
| | 28 | 6 |
| | 29 | 6 |
| | 30 | 6 |
| | 31 | 6 |
| | 32 | 6 |
| Comparative example | 10 | 1 |
| | 11 | 2 |
| | 12 | 2 |
| | 13 | 1 |
| | 14 | 2 |
| | 15 | 2 |

As can be seen from Table 9, when dicarboxylic acid or its salt and a calcium salt having a solubility product constant ($K_{sp}$) of $10^{-5}$ to $10^{-20}$ were used, improvements in dental tubule occlusion capability could be seen from examples 16 through 23. Further, in the case of examples 24 through 32 in which dicarboxylic acid or its salt, a calcium salt having a solubility product constant ($K_{sp}$) of $10^{-5}$ to $10^{-20}$ and phosphate were simultaneously applied, it was found that the occlusion capability further increased by a synergetic effect of the phosphate. This was found consistent with the results of tooth hardness. In contrast, as shown in comparative examples, when only a calcium salt having a solubility product constant ($K_{sp}$) of $10^{-5}$ to $10^{-20}$, when only phosphate was included and when soluble calcium and dicarboxylic acid or its salt were used, the dental tubule occlusion capability was found low. Thus, it was found that when a calcium salt having a solubility product constant ($K_{sp}$) of $10^{-5}$ to $10^{-20}$ and dicarboxylic acid or its salt were applied together, it was effective in occluding the dental tubules, and when phosphate was added thereto, the dental tubule occlusion capability much further increased.

What is claimed is:

1. A method for preventing or reducing tooth sensitivity, comprising applying an oral composition comprising
   i) a dicarboxylic acid selected from the group consisting of malonic acid, succinic acid, glutaric acid, adipic acid, pimelic acid, suberic acid, azelaic acid and mixtures thereof, wherein the dicarboxylic acid is in the form of a salt, and further wherein the salt is a metal ion selected from the group consisting of sodium and potassium;
   ii) a partially soluble calcium salt;
   iii) 1.5-10 wt % phosphate; and
   iv) 0.3-1 wt % pharmaceutical agent,
   wherein the partially soluble calcium salt is calcium carbonate, calcium hydrogen phosphate, calcium sulphite, calcium fluoride, calcium hydroxide, calcium iodate or mixtures thereof, wherein the phosphate is monosodium phosphate, disodium phosphate, trisodium phosphate, monopotassium phosphate, dipotassium phosphate, tripotassium phosphate or mixtures thereof, wherein the pharmaceutical agent is sodium fluoride, sodium monofluorophosphate, stannous fluoride, chlorohexidine, allantoin chlorohydroxyaluminate, aminocaproic acid, pyridoxine hydrochloride, tocopherol acetate, enzymes, or a combination thereof, and wherein a weight ratio of i) the dicarboxylic acid salt; ii) the partially soluble calcium salt; and iii) the phosphate is 1:5-50:1-30 (dicarboxylic acid salt:partially soluble calcium salt:phosphate).

2. The method according to claim 1, wherein the calcium salt is a calcium salt having a solubility product constant ($K_{sp}$) of $10^{-5}$ to $10^{-20}$.

3. The method according to claim 1, wherein the calcium salt is present in an amount of 1 to 50 wt % based on the total weight of the composition.

\* \* \* \* \*